(12) United States Patent
Zolotukhin et al.

(10) Patent No.: US 6,660,514 B1
(45) Date of Patent: *Dec. 9, 2003

(54) METHOD OF PREPARING RECOMBINANT ADENO-ASSOCIATED VIRUS COMPOSITIONS

(75) Inventors: Sergei Zolotukhin, Gainesville, FL (US); Barry J. Byrne, Gainesville, FL (US); Nicholas Muzyczka, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,475

(22) Filed: Jul. 21, 2000

Related U.S. Application Data

(63) Continuation of application No. 09/321,897, filed on May 27, 1999, now Pat. No. 6,146,874.
(60) Provisional application No. 60/086,898, filed on May 27, 1998.

(51) Int. Cl.$^7$ .............................. C12N 7/02; A23J 1/00; C07K 1/00
(52) U.S. Cl. ........................ 435/239; 435/5; 435/235.1; 435/320.1; 435/803; 435/948; 530/412; 530/826
(58) Field of Search .............................. 435/239, 235.1, 435/803, 320.1, 5, 948; 530/412, 826

(56) References Cited

U.S. PATENT DOCUMENTS

| | | | |
|---|---|---|---|
| 5,139,941 A | 8/1992 | Muzyczka et al. | 435/172.3 |
| 5,646,034 A | 7/1997 | Leavitt et al. | 435/325 |
| 5,658,776 A | 8/1997 | Flotte et al. | 435/172.3 |
| 5,681,731 A | 10/1997 | Lebkowski et al. | |

FOREIGN PATENT DOCUMENTS

| | | | |
|---|---|---|---|
| WO | WO 93/24641 | 12/1993 | C12N/5/10 |
| WO | WO 96/39495 | 12/1996 | |
| WO | WO-97/08298 | * 3/1997 | |
| WO | WO98/00524 | 1/1998 | |

OTHER PUBLICATIONS

Dracopoli, Current Protocols in Human Genetics, vol. 10, pp 12.1.1–12.1.24, 1994–1998 by John Wiley & Sons, Inc.*
Hermans, W.T.J.M.C., et al. "Purification of Higher–Titer Adeno–Associated Virus Vectors for Gene Delivery in the Brain," Graduate School for Neurosciences, Netherlands Institute for Brain Research, Amsterdam, The Netherlands.
Zolotukhin, S.; et al. "Recombinant Adeno–Associated Virus Purification Using Novel Methods Improves Infectious Titer and Yield," Gene Therapy (1999) vol. 6, pp. 973–985.
International Search Report for Application No. PCT/US99/11945 dated Oct. 12, 1999.
Anderson and Grinsted, "A new method for the purification of human motile spermatozoa applying density–gradient centrifugation: Polysucrose media compared to percoll media," J. Assis. Reprod. Genet., 14:624–628, 1997.
Bartlett and Samulski, "Fluorescent viral vectors: A new technique for the pharmacological analysis of gene therapy," Nature Med., 4:635–637, 1998.
Basi and Rebois, "Rate zonal sedimentation of proteins in one hour or less," Anal. Biochem., 251:103–109, 1997.
Cartwright et al., "Investigation of the role of lipids in the assembly of very low density lipoproteins in rabbit hepatocytes," J. Lipid Res., 38:531–545, 1997.
Chiorini et al., "High–efficiency transfer of the T cell co–stimulatory molecule B7-2 to lymphoid cells using high–titer recombinant adeno–associated virus vectors," Hum. Gene Ther. 6:1531–1541, 1995.
Clark et al., "Cell lines for the production of recombinant Adeno–associated virus," Hum. Gene Ther. 6:1329–1341. 1995.
Clark et al., "Highly purified recombinant adeno–associated virus vectors are biologically active and free of detectable helper and wild–type viruses," Hum. Gene Ther., 10:1031–1039, 1999.
Conway et al., "Recombinant Adeno–associated virus Type 2 replication and packaging is entirely supported by a Herpes Simplex virus Type 1 amplicon expressing rep and cap," J. Virol. 71:8780–8789, 1997.
Ferrari et al., "New developments in the generation of Ad–free, high–titer rAAV gene therapy vectors," Nature Med., 3:1295–1297, 1997.
Graham et al., "A novel method for the rapid separation of plasma lipoproteins using self–generating gradients of iodixanol," Atherosclerosis, 124:125–135, 1996.
Grimm et al., "Novel tools for production and purification or recombinant AAV vectors," Hum. Gene Ther. 9:2745–2760, 1998.
Hermonat and Muzyczka, "Use of adeno–associated virus as a mammalian DNA cloning vector: transduction of neomycin resistance into mammalian tissue culture cells," Proc. Natl. Acad. Sci. USA 81:6466–6470, 1984.
Herold et al., "Identification of structural features of heparin required for inhibition of Herpes Simplex virus Type 1 binding," Virol. 206:1108–1116, 1995.
Inoue and Russell, "Packaging cells based on inducible gene amplification for the production of adeno–associated virus vectors," J Virol. 72:7024–7031, 1998.

(List continued on next page.)

Primary Examiner—Mary K. Zeman
(74) Attorney, Agent, or Firm—Williams, Morgan & Amerson, P.C.

(57) ABSTRACT

Disclosed are methods for the isolation and purification of high-titer recombinant adeno-associated virus (rAAV) compositions. Also disclosed are methods for reducing or eliminating the concentration of helper adenovirus in rAAV samples. Methods are disclosed that provide highly-purified rAAV stocks having titers up to about $10^{13}$ particles/ml at particle-to-infectivity ratios of less than 100 in processes that are accomplished about 24 hours or less.

28 Claims, 3 Drawing Sheets

OTHER PUBLICATIONS

Figure 1:
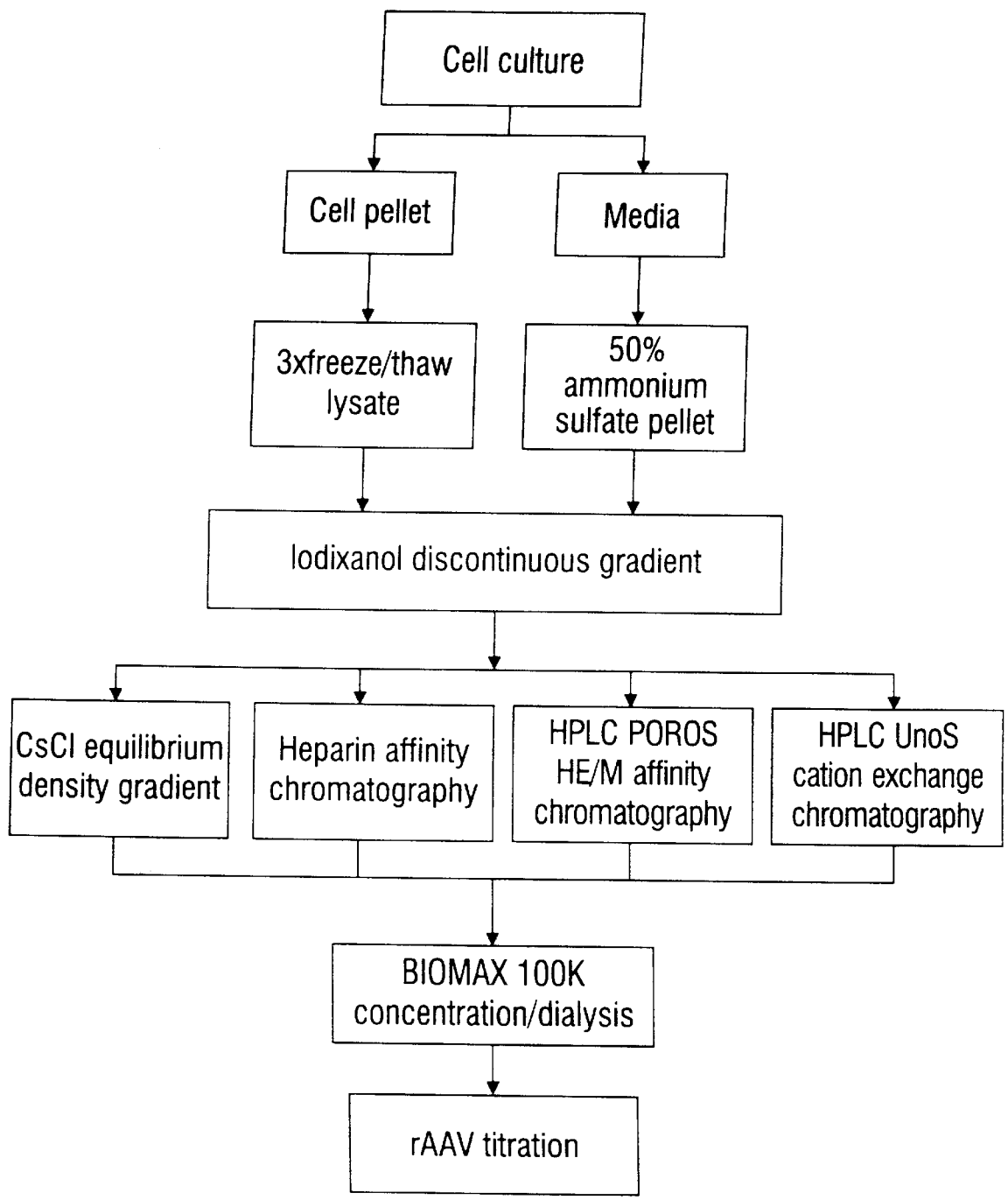

Klein, "Neuron–specific transduction in the rat septohippocampal or nigrostriatal pathway by recombinant adeno–associated virus vectors," *Exper. Neurol.* 150:183–194, 1998.

Lewin et al., "Ribozyme rescue of photoreceptor cells in a transgenic rat model of autosomal dominant retinitis pigmentosa," *Nat. Med.* 4:967–971, 1998.

Li et al., "Role for highly regulated rep gene expression in adeno–associated virus vector production," *J. Virol.* 71:5236–5243, 1997.

Maxwell et al., "Improved production of recombinant AAV by transient transfection of NB324K cells using electroporation," *J. Virol. Methods*, 63:129–136, 1997.

Neyts et al., "Sulfated polymers inhibit the interaction of human cytomegalovirus with cell surface heparan sulfate," *Virology* 189:48–58, 1992.

Peel, "Efficient transduction of green fluorescent protein in spinal cord neurons using adeno–associated virus vectors containing cell type–specific promoters," *Gene Ther.* 4:16–24, 1997.

Salvetti, "Factors influencing recombinant adeno–associated virus production," *Hum. Gene Ther.* 9:695–706, 1998.

Sasagawa et al., "Synthesis and assembly of virus–like particles of human papillomaviruses type 6 and type 16 in fission yeast *Scizosaccharomyces pombe*," *Virology*, 206:126–135, 1995.

Snyder et al., "Production of recombinant adeno–associated viral vectors," *In: Current Protocols in Human Genetics* (eds. Dracopoli et al.), John Wiley, New York, 1996.

Summerford and Samulski., "Membrane–associated heparan sulfate proteoglycan is a receptor for adeno–associated virus type 2 virions," *J. Virol.* 72:1438–1445, 1998.

Tamayose et al., "A new strategy for large–scale preparation of high–titer recombinant adeno–associated virus by using packaging cell lines and sulfonated cellulose column chromatography," *Hum. Gene Ther.* 7:507–513, 1996.

van der Burg et al., "No porcine islet loss during density gradient purification in a novel iodixanol in University of Wisconsin solution,"*Transplant. Proc.*, 30:362–363, 1998.

Xiao et al., "Production of high–titer recombinant adeno–associated virus vectors in the absence of helper Adenovirus," *J. Virol.* 72:2224–2232, 1998.

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:SYNTHETIC

<400> SEQUENCE: 1
tatgggatcg gccattgaac                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:SYNTHETIC

<400> SEQUENCE: 2
cctgatgctc ttcgtccaga                                                  20
```

US 6,660,514 B1

METHOD OF PREPARING RECOMBINANT ADENO-ASSOCIATED VIRUS COMPOSITIONS

This application is a continuation of U.S. application Ser. No. 09/321,897, filed May 27, 1999, now U.S. Pat. No. 6,146,874.

The present application claims the priority of U.S. Provisional Patent Application Ser. No. 60/086,898 filed May 27, 1998, the entire disclosure of which is incorporated herein by reference without disclaimer.

The government may have certain rights in the present invention pursuant to grant numbers PO1 HL59412 and PO1 NS36302 from the National Institutes of Health.

BACKGROUND OF THE INVENTION

1.1 Field of the Invention

The present invention relates generally to the field of virology, and in particular, to methods for preparing highly-purified, high-titer recombinant adeno-associated virus compositions. In certain embodiments, the invention concerns the use of equilibrium density centrifugation techniques, affinity chromatographic media, and in certain embodiments anion- and cation-exchange resins, to remove rAAV particles from solution and to prepare highly purified viral stocks for use in a variety of investigative, diagnostic and therapeutic regimens. Methods are also provided for purifying rAAVs from solution and for reducing the concentration of adenovirus in rAAV stocks.

1.2 Description of Related Art
1.2.1 Adeno-Associated Virus

Adeno-associated virus-2 (AAV) is a human parvovirus which can be propagated both as a lytic virus and as a provirus (Cukor et al., 1984; Hoggan et al., 1972). The viral genome consists of linear single-stranded DNA (Rose et al., 1969), 4679 bases long (Srivastava et al., 1983), flanked by inverted terminal repeats of 145 bases (Lusby et al., 1982). For lytic growth AAV requires co-infection with a helper virus. Either adenovirus (Ad; Atchinson et al., 1965; Hoggan, 1965; Parks et al., 1967) or herpes simplex virus (HSV; Buller et al., 1981) can supply helper function. Without helper, there is no evidence of AAV-specific replication or gene expression (Rose et al., 1972; Carter et al., 1983; Carter et al., 1983). When no helper is available, AAV can persist as an integrated provirus (Hoggan, 1965; Berns et al., 1975; Handa et al., 1977; Cheung et al., 1980; Berns et al., 1982).

Integration apparently involves recombination between AAV termini and host sequences and most of the AAV sequences remain intact in the provirus. The ability of AAV to integrate into host DNA is apparently an inherent strategy for insuring the survival of AAV sequences in the absence of the helper virus. When cells carrying an AAV provirus are subsequently superinfected with a helper, the integrated AAV genome is rescued and a productive lytic cycle occurs (Hoggan, 1965).

AAV sequences cloned into prokaryotic plasmids are infectious (Samulski et al., 1982). For example, when the wild type AAV/pBR322 plasmid, pSM620, is transfected into human cells in the presence of adenovirus, the AAV sequences are rescued from the plasmid and a normal AAV lytic cycle ensues (Samulski et al., 1982). This renders it possible to modify the AAV sequences in the recombinant plasmid and, then, to grow a viral stock of the mutant by transfecting the plasmid into human cells (Samulski et al., 1983; Hermonat et al., 1984). AAV contains at least three phenotypically distinct regions (Herrnonat et al., 1984). The rep region codes for one or more proteins that are required for DNA replication and for rescue from the recombinant plasmid, while the cap and lip regions appear to code for AAV capsid proteins and mutants within these regions are capable of DNA replication (Hermonat et al., 1984). It has been shown that the AAV termini are required for DNA replication (Samulski et al., 1983).

The construction of two *E. coli* hybrid plasmids, each of which contains the entire DNA genome of AAV, and the transfection of the recombinant DNAs into human cell lines in the presence of helper adenovirus to successfully rescue and replicate the AAV genome has been described (Laughlin et al., 1983; Tratschin et al., 1984a; 1984b).

1.2.2 Conventional Methods for Preparing Recombinant AAV

Recombinant adeno-associated virus (rAAV) has been demonstrated to be a useful vector for efficient and long-term gene transfer in a variety of tissues, including lung (Flotte, 1993), muscle (Kessler, 1996; Xiao and Samulski, 1996; Clark et al., 1997; Fisher et al., 1997), brain (Kaplitt, 1994; Klein, 1998) retina (Flannery, 1997; Lewin et al., 1998), and liver (Snyder, 1997). It has also been demonstrated to evade the immune response of the host by failing to transduce dendritic cells (Jooss et al., 1998). Phase I clinical trails are underway for cystic fibrosis rAAV-mediated gene therapy (Flotte et al., 1996; Wagner et al., 1998). Yet in spite of these promising developments one of the problems that remains to be solved is that vector production remains very laborious.

Currently rAAV is most often produced by co-transfection of rAAV vector plasmid and wt AAV helper plasmid into Ad-infected 293 cells (Hermonat and Muzyczka, 1984). Recent improvements in AAV helper design (Li et al., 1997) as well as construction of non-infectious mini-Ad plasmid helper (Grimm et al., 1998; Xiao et al., 1998; Salvetti, 1998) have eliminated the need for Ad infection, and made it possible to increase the yield of rAAV up to $10^5$ particles per transfected cell in a crude lysate. Scalable methods of rAAV production that do not rely on DNA transfection have also been developed (Chiorini etal., 1995; Conway etal., 1997; Inoue and Russell, 1998; Clark etal., 1995). These methods, which generally involve the construction of producer cell lines and helper virus infection, are suitable for high-volume production.

However, little progress has been made on the downstream purification of rAAV. The conventional protocol involves the stepwise precipitation of rAAV using ammonium sulfate, followed by two or preferably, three rounds of CsCl density gradient centrifugation. Each round of CsCl centrifugation involves fractionation of the gradient and probing fractions for rAAV by dot-blot hybridization or by PCR™ analysis. No only does it require two weeks to complete, but the current protocol often results in poor recovery of the vector and poor virus quality. The growing demand for different rAAV stocks often strains the limited capacities of vector production facilities. There is, therefore, a clear need for a protocol that will reduce the preparation time substantially without sacrificing the quality and/or purity of the final product.

2.0 SUMMARY OF THE INVENTION

In a first embodiment, the invention concerns a method of purifying a recombinant adeno-associated virus. In general, the method comprises centrifuging a sample containing or suspected of containing recombinant adeno-associated virus through at least a first iodixanol gradient, and collecting the purified virus or at least a first fraction comprising the recombinant adeno-associated virus, from the gradient. Preferably the gradient is a discontinuous gradient, although the inventors contemplate the formulation of continuous iodixanol gradients that also provide purification of rAAV compositions. In certain aspects of the invention, multiple iodixanol gradients, for example at least a second, at least a third and/or at least a fourth iodixanol gradient, are used to purify the recombinant adeno-associated virus.

In an exemplary discontinuous iodixanol gradient, the gradient comprises an about 15% iodixanol step, an about 25% iodixanol step, an about 40% iodixanol step, and an about 60% iodixanol step. Optionally, the gradient may contain steps having lower concentrations of iodixanol, and likewise, the gradient may contain steps that have higher concentrations of iodixanol. Naturally, the concentrations of each step do not need to be exact, but can vary slightly depending upon the particular formulation and preparation of each step. The inventors have shown that most rAAV particles will band in an iodixanol gradient at a level corresponding to a percentage of iodixanol approximately equal to 52%, although depending upon the number of viral particles loaded on the gradient and the volume and capacity of the gradient, the range of concentrations at which purified rAAV particles may be found may range on the order of from about 50% to about 53%, or from about 50% to about 54%, 55%, 56%, 57%, 58%, 59% and even up to and including about 60% iodixanol. Likewise, the range of concentrations at which the rAAV particles may be isolated following centrifugation may be on the order of from about 55% down to and including about 49%, about 48%, about 47%, about 46%, about 45%, about 44%, about 43%, about 42%, about 41% or about 40% or so iodixanol. Naturally, all concentrations in the range of from about 40% to about 60% are contemplated to be useful in recovering purified rAAV particles from the centrifuged gradient. As such, all intermediate concentrations including about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, and about 59% or so are contemplated to be useful in the practice of the present invention for recovering purified rAAV particles from the centrifuged gradient.

When step gradients are utilized, it is convenient to include in the gradient steps that encompass or "bracket" the range of optimal recovery of virus. For example, in a 25%/40%/60% step gradient, the 40% band comprises the virus, and this fraction is then removed for recovery of the virus composition. The design of both continuous and discontinuous gradients is well-known to those of skill in the art, and those having benefit of the present specification may readily prepare iodixanol gradients of sufficient capacity and range to isolate a band of purified rAAV particles from the gradient following centrifugation.

In certain embodiments, to improve the yield and/or recovery of virus particles from such a gradient, one may add to one or more steps of the gradient one or more salts to reduce or prevent aggregation of the virus and any cellular debris or proteins, polypeptides, etc. which may be present in the crude sample. In an exemplary embodiment, the inventors have shown that the addition of salt to the 15% iodixanol step in a discontinuous gradient improves the recovery of virus particles from an iodixanol gradient. As an example, the addition of NaCl to a final concentration of about 1 M in the 15% step was found by the inventors to be particularly advantageous in recovery of purified rAAV particles from the 40% step of such a gradient. While addition of one or more salts to one or more of the other steps in the gradient may be performed as required, in most instances, the inventors have shown that the presence of salt in other steps were either unnecessary or unwarranted. In situations where one or more salts are added to a layer which comprises the rAAV particles, following centrifugation it may be desirable to remove or reduce the concentration of salt in such a fraction prior to use of, or further purification of, the rAAV. Such removal may readily be achieved by dialysis, microconcentration, ultrafiltration, and the like.

In alternative embodiments, the inventors contemplate that the gradient may optionally comprise one or more additional compositions to permit farther, or enhanced purification of rAAV particles. Such compositions may include derivatives of iodixanol, iodixanol analogs, iodixanol-derived compounds, and/or compounds having centrifugation properties similar to, equal to, or superior to, iodixanol-alone compositions. Depending upon the particular composition added to the gradient, the relative position of the purified particles in the gradient may vary from that in which iodixanol alone is used (i.e. approximately 52% iodixanol), but such variance is readily overcome in the design of the gradient, and does not preclude the isolation of the rAAV from the particular density in the gradient where such virus particles are banded following centrifugation. Likewise, when one or more compositions are added to the iodixanol gradient, the centrifugation time, centrifugal force, and/or banding position within the gradient of the viral particles may be varied depending upon the particular application. Any such variations, improvements, or alterations in the composition of the iodixanol gradient are also contemplated to fall within the scope of this invention, and such modifications to the gradient will be apparent to those of skill in the art given the benefit of the teachings of the instant specification.

In a second embodiment, the invention relates to a method for purifying rAAV particles that comprises contacting a sample containing the virus with at least a first matrix that comprises heparin, under conditions effective and for a period of time sufficient to permit binding of the virus to the matrix, removing any unbound proteins or contaminants from the matrix, and then subsequently collecting or eluting the virus from the matrix. In exemplary embodiments, the matrix comprises heparin agarose type I or heparin agarose type II-S, although the inventors contemplate the use of any heparin composition or combinations thereof demonstrated to be effective in binding the rAAV, and thus removing it from a solution that is contacted with such a matrix. Preferably, the matrix is an affinity chromotographic medium, that may be comprised within a column, a syringe, a microfilter, or microaffinity column, or alternatively may be comprised within an HPLC affinity column. The matrix may be formed of any material suitable for the preparation of a heparin affinity matrix, and may, for example, be formulated as a resin, bead, agarose, acrylamide, glass, fiberglass, plastic, polyester, methacrylate, cellulose, sepharose, sephacryl, and/or the like. In fact, the inventors contemplate that the matrix may be fashioned out of any suitable material that forms a solid or semi solid support, and that permits the adsorption, ionic bonding, covalent linking, crosslinking, derivatization, or other attachment of a heparin moiety to the support matrix. Indeed, the art of affinity chromatographic medium preparation is sufficiently advanced so that a skilled artisan could readily prepare a suitable heparin affinity medium for use in purifying the rAAV particles using the methods disclosed herein. For example, the inventors have shown that an HPLC affinity column containing a crosslinked polyhydroxylated polymer derivatized with one or more heparin functional groups was useful in the purification of rAAV from a solution contacted with such a column.

Elution of the bound virus to the affinity column may be achieved in any manner convenient to the skilled practitioner, and may include, for example, the use of one or more elution buffers such as a salt buffer, to collect the virus from the column. In an exemplary embodiment, the inventors utilized a 1 M NaCl solution to elute the virus from the column. Prior to elution, the column comprising the bound virus may be washed with one or more washing or equilibrating buffers prior to elution of the virus from the column.

The use of an affinity column to purify rAAV particles may be used alone, or may be combined with the iodixanol gradient as described above to further increase the purification of the rAAV composition. One or more affinity columns may be utilized prior to the density gradient centrifugation purification method, and/or one or more affinity columns may be utilized after the purification through iodixanol gradients. In an exemplary embodiment, a cellular lysate containing rAAV particles is subjected to iodixanol centrifligation, and the fraction of the gradient containing the partially-purified rAAV is then contacted with at least one heparin affinity column to increase the total purity of the rAAV preparation.

Likewise, following either or both of the aforementioned purification methods, the rAAV composition obtained may be subjected to further purification, dialysis, concentration, and/or the like. In an exemplary embodiment, the partially-purified rAAV preparation may be further purified by contacting a fraction or sample containing or comprising recombinant adeno-associated virus with a hydrophobic matrix, under conditions effective to permit interaction of hydrophobic species (proteins or other contaminants) with the hydrophobic matrix, and collecting the non-interacting virus from the hydrophobic matrix. Preferred are hydrophobic matrices that comprise phenyl groups, for example phenyl sepharose, phenyl sepharose 6 fast flow (low sub) or phenyl sepharose 6 (high sub). In certain embodiments, rAAV that has been partially purified by heparin affinity chromatography is further purified by hydrophobic interaction chromatography.

In other embodiments, the partially-purified rAAV preparation may be further purified by subjecting the viral sample to one or more cesium chloride equilibrium density gradients, and collecting from the gradient(s) the fraction(s) comprising the purified virus. The virus may then optionally be further purified by dialysis, microfiltration, microconcentration, and/or precipitation. Additionally, the virus may be further purified by contacting the virus with one or more ion exchange chromatography media, and eluting the virus from the media using one or more suitable elution buffers. Such an ion exchange chromatography medium may comprise a cation or an anion exchange medium. An exemplary cation exchange medium comprises at least one negatively-charged sulfonic group.

Contaminants that may be present in the sample containing the recombinant adeno-associated virus include, but are not limited to, viruses, such as adenovirus or herpes simplex virus, proteins, polypeptides, peptides, nucleic acids, cell extracts, growth medium, or combinations thereof. The methods of the present invention serve to reduce or eliminate one or more, or in certain embodiments all of the contaminants in a given recombinant adeno-associated virus sample. In preferred embodiments, the rAAV is about 70%, about 80%, about 90%, about 95%, about 98%, about 99%, about 99.5% or more pure as judged by any of a variety of assays and analytical techniques that are known to those of skill in the art, including, but not limited to gel electrophoresis and staining and/or spectroscopy.

In certain embodiments, the invention provides methods for the preparation of highly-purified rAAV compositions comprising greater than about $10^{10}$ rAAV particles/ml. In exemplary embodiments, such methods have been demonstrated useful in the preparation of viral compositions comprising greater than about $10^{11}$, $10^{12}$, and even greater than about $10^{13}$ or $10^{14}$ particles/ml. In other embodiments, the invention provides methods for the preparation of rAAV compositions having a particle-to-infectivity ratio of less than about 100, and in certain aspects less than about 90, about 80, about 70, about 60, about 50 about 40, about 30, about 20 about 10, about 5, or in certain exemplary embodiments rAAV compositions having a particle-to-infectivity ratio of about 1.

The process for preparing highly-purified and/or highly-infectious viral preparations generally comprise the steps of centrifuging a sample containing recombinant adeno-associated virus through an iodixanol gradient, collecting from the iodixanol gradient at least a first fraction comprising the recombinant adeno-associated virus, contacting the at least a first fraction comprising the recombinant adeno-associated virus with a matrix comprising heparin, under conditions effective to permit binding of the virus to the matrix, removing non-bound species from the matrix, and eluting the virus from the matrix. Other methods for isolating rAAV provided by the present invention comprise the steps of centrifuging a sample containing or suspected of containing recombinant adeno-associated virus through an iodixanol gradient, collecting the purified virus from the gradient, contacting the virus collected from the gradient with a matrix comprising heparin, under conditions effective to permit binding of the virus to the matrix, collecting the virus from the matrix, subjecting the virus collected from the matrix to at least a first cesium chloride equilibrium density gradient, and collecting from the gradient a fraction comprising the highly-purified rAAV composition.

Additional methods of isolating a recombinant adeno-associated virus are also provided in the present invention. These methods generally comprises the steps of centrifuging a sample containing recombinant adeno-associated virus through an iodixanol gradient, collecting from the iodixanol gradient at least a first fraction comprising the recombinant adeno-associated virus, contacting the at least a first fraction comprising the recombinant adeno-associated virus with a matrix comprising heparin, under conditions effective to permit binding of the virus to the matrix, removing at least a first non-bound species from the matrix, eluting the virus from the matrix, contacting the eluted virus with a hydrophobic matrix, under conditions effective to permit interaction of hydrophobic species with the hydrophobic matrix, and collecting the non-interacting virus from the hydrophobic matrix.

Further methods generally comprise the steps of centrifuging a sample suspected of containing recombinant adeno-associated virus through an iodixanol gradient, collecting the purified virus from the gradient, contacting the virus collected from the gradient with a first matrix comprising heparin, under conditions effective to permit binding of the virus to the matrix, collecting the virus from the first matrix, contacting the virus collected from the first matrix with a second matrix comprising an anion exchange medium, and collecting from the second matrix a fraction comprising the purified virus.

In another embodiment, the invention provides a method of preparing recombinant adeno-associated virus. The method generally involves subjecting a sample suspected of containing recombinant adeno-associated virus to centrifugation through an iodixanol gradient, and collecting the virus from a fraction of the gradient corresponding to a concentration of iodixanol of about 40%. Such a gradient may be formed as described above, and may be prepared either as a continuous or a discontinuous gradient. In the case of discontinuous gradients, the gradient will preferably include at least an about 15% iodixanol step, an about 25% iodixanol step, an about 40% iodixanol step, and an about 60% iodixanol step, with the virus being isolatable from the 40% iodixanol step following centrifugation. Following recovery of the banded rAAV particles, the virus may be further purified using the heparin affinity chromatographic methods disclosed herein, and/or be optionally further purified via CsCl gradient centrifugation, anion exchange chromatography, cation exchange chromatography, affinity chromatography, or precipitation.

The invention also provides methods for reducing or eliminating adenovirus from a recombinant adeno-associated virus composition contaminated with adenovirus. The method generally comprises centrifuging a sample containing or suspected of containing both recombinant adeno-associated virus and adenovirus through one or more iodixanol gradients as described herein, and collecting the recombinant adeno-associated virus from the gradient. The concentration of adenovirus may be further reduced in such a sample by a number of methods, including, but not limited to, further purification on a heparin affinity column and/or a hydrophobic interaction column, by heating the sample, or alternatively, by anion exchange chromatography as described herein.

A method for reducing the concentration of adenovirus in a recombinant adeno-associated virus composition is also provided that generally involves centrifuging a sample containing recombinant adeno-associated virus through an iodixanol gradient, collecting from the iodixanol gradient at least a first fraction comprising the recombinant adeno-associated virus, contacting the at least a first fraction comprising the recombinant adeno-associated virus with a matrix comprising heparin, under conditions effective to permit binding of the virus to the matrix, removing any non-bound species from the matrix, and eluting the virus from the matrix.

A further aspect of the invention is the preparation of a high-titer rAAV composition. The method generally comprises the steps of: centrifuging a sample or rAAV through an iodixanol gradient, collecting the purified recombinant adeno-associated virus from the gradient; contacting the partially-purified recombinant adeno-associated virus collected from the gradient with a matrix comprising heparin, under conditions effective to permit binding of the recombinant adeno-associated virus to the matrix, and collecting the recombinant adeno-associated virus from the matrix. The purified rAAV composition eluted from the matrix may also be optionally further purified, such as in the case of the preparation of high-titer viral stocks, by contacting :the sample with a matrix comprising an anion exchange medium, under conditions effective to permit binding of the recombinant adeno-associated virus to the matrix, and collecting the purified recombinant adeno-associated virus from the matrix, preferably by elution.

The present invention thus also provides recombinant adeno-associated virus compositions, prepared by any one or more of the methods described herein. Generally, the invention provides at least a first recombinant adeno-associated virus composition, prepared by applying a sample containing recombinant adeno-associated virus to an iodixanol gradient, and collecting from the gradient at least a first fraction comprising the recombinant adeno-associated virus.

Also provided by the present invention are kits comprising combinations of the recombinant adeno-associated virus isolation media described herein. Generally, the kits comprise, in a suitable container, iodixanol and a matrix comprising heparin. In certain preferred aspects, the iodixanol is formulated as an iodixanol gradient. In other kits of the present invention, the matrix comprises heparin agarose type I or heparin agarose type II-S. Additional kits of the invention further comprise a hydrophobic matrix, such as a matrix comprising phenyl groups, exemplified by phenyl sepharose.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. rAAV purification flow chart.

Figure 2:
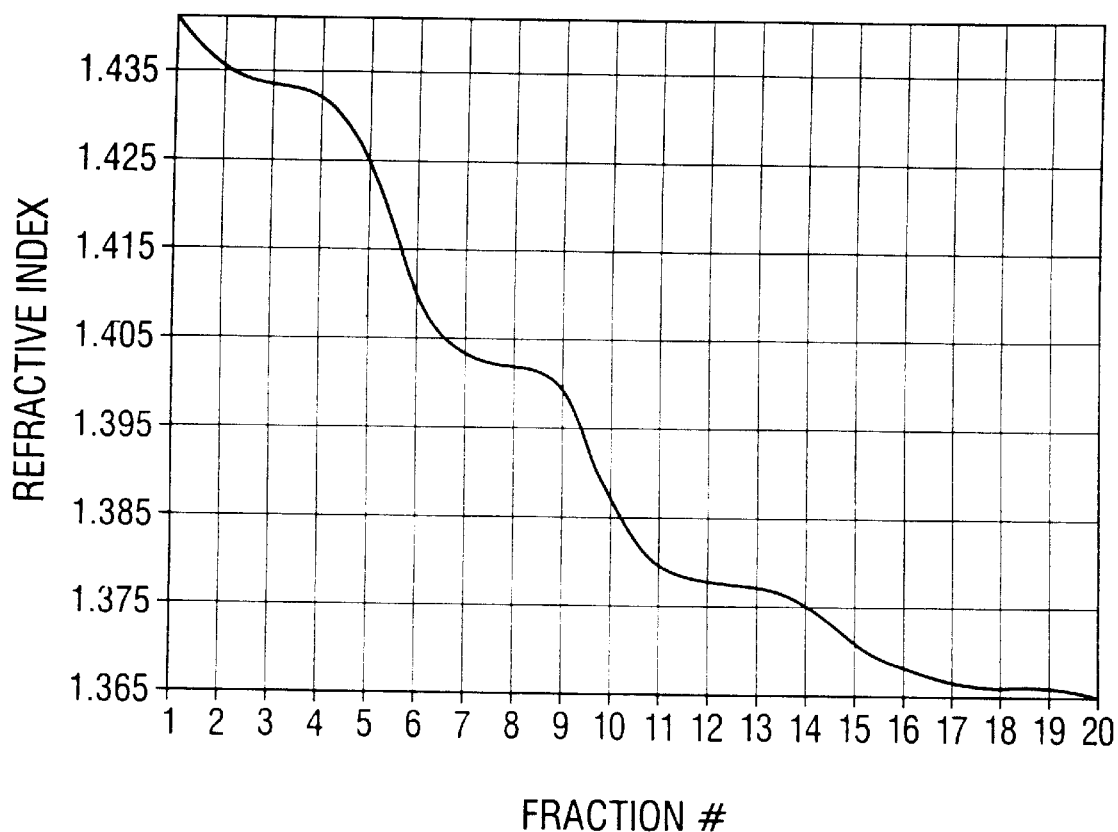

FIG. 2. Iodixanol step gradient for the purification of rAAV. Shown is a plot of the refractive index (vertical axis) of one ml-fractions (fraction number, horizontal axis) collected from the bottom of a tube after a 1 hour spin.

Figure 3A:
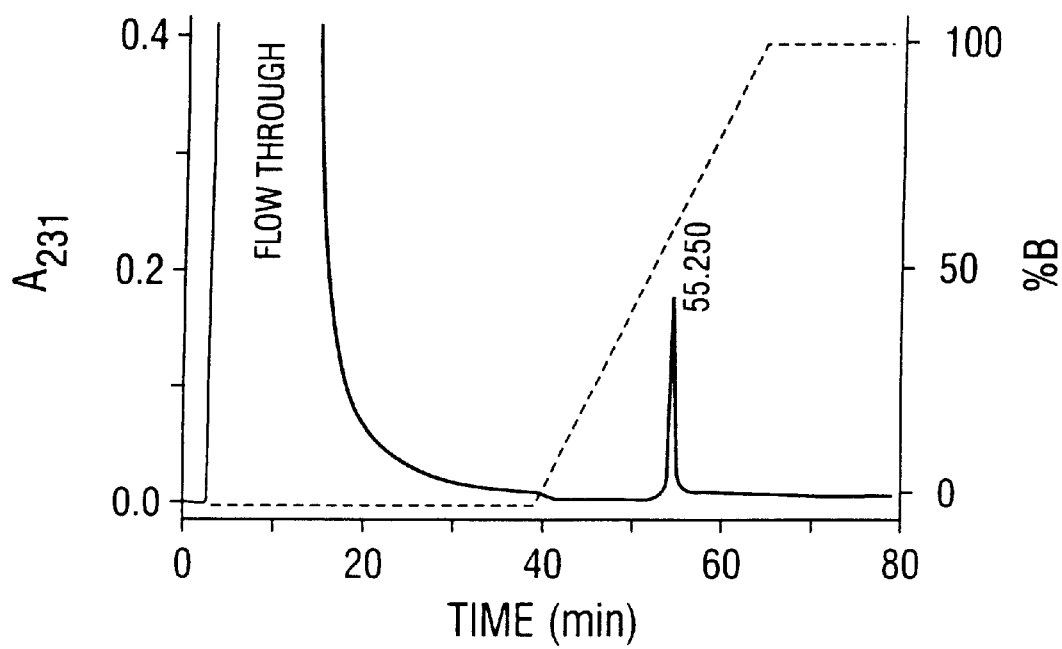
Figure 3B:
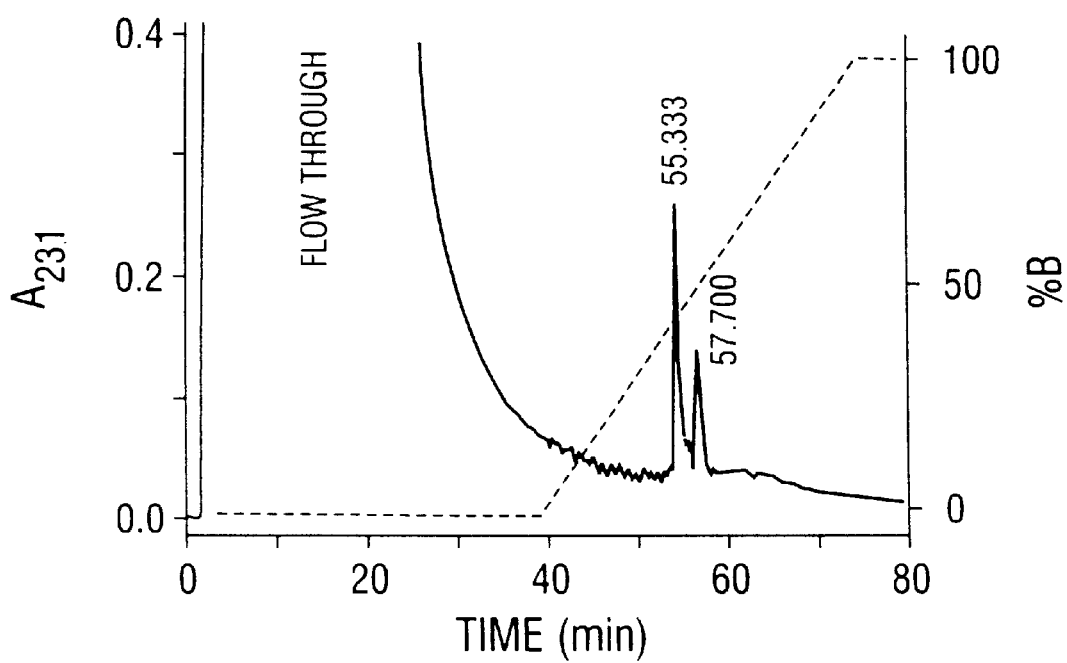

FIG. 3A and FIG. 3B. HPLC purification of the iodixanol fraction of rAAV-UF5, monitored at 231 nm. The absorbance at 231 nm ($A_{231}$) is shown on the left vertical axis, time (min) is shown on the horizontal axis, and the ratio of diluent B (%B) is shown on the right vertical axis. FIG. 3A. POROS® HE/M chromatography. FIG. 3B. UNO™ S1 cation exchange chromatography. The dotted line indicates the shape of the gradient. Elution time is shown in min above the respective peaks.

4.0 DESCRIPTION OF ILLUSTRATIVE EMBODIMENTS

Recently, it has been shown that the transduction of cells by wt AAV was mediated through the heparan sulfate proteoglycan receptor (Summerford and Samulski, 1998). In order to develop an efficient and simple protocol for purification of rAAV, the inventors developed heparin affinity column chromatography, which significantly simplifies and expedites the production of rAAV. To efficiently bind the virus to the affinity media the inventors have also introduced a new pre-purification technique—centrifuigation of the crude viral lysate through a pre-formed gradient of the non-ionic gradient media iodixanol. The present invention provides for the first time protocols which permit the completion of rAAV purification in one day and produces viral stocks sufficiently pure for pre-clinical and/or clinical studies. The inventors have shown that use of these new purification techniques permit an increase in the yield of purified virus by at least 10-fold over conventional methods, resulting in highly-purified, high-titer stocks ($10^{12}$–$10^{13}$ particles/ml), equivalent to at least about $10^4$–$10^5$ particles per cell, as well as improved viral infectivity and more rapid purification.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Methods for Production of rAAV Compositions

5.1.1 Materials and Methods

5.1.1.1 Cells

Low passage number (P29–35) 293 cells were propagated in DMEM/10% FBS. The C12 cell line (Clark et al., 1995) was maintained in the presence of 0.5 mg/ml G418, while the Cre8 cell line (Hardy et al., 1997) was propagated in DMEM supplemented with 200 µg/ml G418.

5.1.1.2 Construction of Recombinant Plasmids

The construction of pTR-UF5 was described earlier (Klein, 1998). To produce the vector containing the enhanced blue fluorescent mutant of green fluorescent protein (gfp; Heim and Tsien, 1996), the inventors have introduced the Tyr-145-Phe mutation into pTR-UFB background (Zolotukhin et al., 1996) using Quick Change site-Directed Mutagenesis kit (Stratagene, La Jolla, Calif.). The resulting plasmid was termed pTR-UF6. To construct the rAd-UF7 vector, the inventors substituted the rAAV cassette from pTR-UF5 for the CMV promoter fragment in pAdlox (Hardy et al., 1997). The infectious rAd-UF7 was rescued essentially as described by Hardy et al. (1997). QC-PCR™ standard template pdl-neo was constructed as described earlier (Conway et al., 1997). The primers used to detect rAAV were:

5'-TATGGGATCGGCCATTGAAC-3' (SEQ ID NO:1) and

5'-CCTGATGCTCTTCGTCCAGA-3' (SEQ ID NO:2).

5.1.1.3 Production of rAAV

To produce rAAV, a triple co-transfection procedure was used to introduce a rAAV vector plasmid (pTR-UF5 or pTR-UF6) together with pACG2 AAV helper (Li et al., 1997) and pXX6 Ad helper (Xiao et al., 1998) at a 1:1:1 molar ratio. Alternatively, rAAV vector plasmid was co-transfected with the helper plasmid pDG carrying the AAV rep and cap genes, as well as Ad helper genes, required for rAAV replication/packaging (Grimm et al., 1998). Plasmid DNA used in the transfection was purified by conventional alkaline lysis/CsCl gradient protocol.

The transfection was carried out as follows: 293 cells (P33) were split 1:2 the day prior to the experiment, so that, when transfected, the cell confluence was about 75–80%. Ten 15-cm plates were transfected as one batch. To make $CaPO_4$-precipitate 180 µg of pACG2 were mixed with 180 µg of pTR-UF5 and 540 µg of pXX6 in a total volume of 12.5 ml of 0.25 M $CaCl_2$. The old media was removed from the cells and the formation of the $CaPO_4$-precipitate was initiated by adding 12.5 ml of 2×HBS pH 7.05 (pre-warmed at 37° C.) to the DNA/$CaCl_2$ solution. The DNA was incubated for 1 min, at which time the formation of the precipitate was stopped by transferring the mixture into pre-warmed 200 ml of DMEM-10% FBS. Twenty-two ml of the media was immediately dispensed into each plate and cells were incubated at 37° C. for 48 h. The $CaPO_4$-precipitate was allowed to stay on the cells during the whole incubation period without compromising cell visibility.

Forty-eight hours post-transfection cells were harvested by centrifugation at 1,140×g for 10 min; the media was discarded unless specified otherwise. Cells were then lysed in 15 ml of 0.15 M NaCl–50 mM Tris HCl pH 8.5 by 3 freeze/thaw cycles in dry ice-ethanol and 37° C. baths. Benzonase (Nycomed Pharma A/S, pure grade) was added to the mixture (50 U/ml final concentration) and the lysate was incubated for 30 min at 37° C. The crude lysate was clarified by centrifugation at 3,700×g for 20 min and the virus-containing supernatant was further purified by iodixanol density gradient centrifugation.

5.1.1.4 Conventional Purification Protocol rAAV was purified essentially as described earlier (Snyder et al., 1996) with the following modifications. The virus pellet after the second ammonium sulfate cut was resuspended in total of 39 ml of 1.37 g/ml CsCl/PBS and subjected to an 18 h spin in 60 Ti rotor (Beckman Instruments, Somerset, NJ) at 255,600×g at 15° C. The gradient was fractionated from the bottom of the tube and aliquots of the middle ten fractions were screened for rAAV by PCR™. Positive fractions were pooled, diluted to 13 ml with the CsCl solution of the same density and centrifuged in an 80 Ti rotor (Beckman Instruments, Somerset, N.J.) at 391,600×g for 3.5 h at 15° C. After fractionation of the gradient, the positive fractions were identified by PCR™ and pooled. The virus then was concentrated/dialyzed using the ULTRAFREE-15 centrifugal filter device BIOMAX-100K (Millipore, Bedford, Mass.).

5.1.1.5 Preparation of Iodixanol Density Gradient

A typical discontinuous step gradient was formed by underlayering and displacing the less dense cell lysate with Iodixanol 5,5'[(2-hydroxy-1-3-propanediyl)-bis (acetylamino]bis[N,N'-bis[2,3dihydroxypropyl-2,4,6-triiodo-1,3-benzenecarboxamide], prepared using the 60% (w/v) sterile solution of OptiPrep (Nycomed). Specifically, 15 ml of the clarified lysate were transferred into a Quick-Seal Ultra-Clear 25×89 mm centrifuge tube (Beckman Instruments, Somerset, N.J.) using a syringe equipped with a 1.27×89 mm spinal needle. Care was taken to avoid bubbles, which would interfere with subsequent filling and sealing of the tube. A two-channel variable speed peristaltic pump, Model EP-1 (Bio-Rad Laboratories, Hercules, Calif.), was equipped with PharMed 1.6 mm ID tubing with two additional 15 cm pieces of silicon 1.6 mm ID tubing attached at both sides of the pump head frame assembly. Each tubing line was equipped at both sides with a 100 µl microcapillary borosilicate glass pipet (Fisher, Pittsburgh, Pa.). Two pipets at one end of both channels were simultaneously placed into 50 ml screw cap conical tubes (Sarstedt).

Eighteen ml of the solution (9 ml per one centrifuge tube) containing 15% iodixanol-1 M NaCl-PBS-MK (1×PBS-1 mM $MgCl_2$, 2.5 mM KCl) were transferred into the tube and the pump was started at 4 ml/min. Both channels were primed with the iodixanol solution down to the tip of the glass pipet at the other end of the line, at which time the pump was stopped and the two pipets were inserted into two centrifuge tubes containing cell lysate. The tips of the pipets were placed at the bottom of the tubes and the pump was started to dispense the first density step. Care was taken to introduce no air bubbles into the tubing, which could disturb the density layers. With about a drop of the first density step solution left in the tube the pump was stopped and 12 ml of the second density step (6 ml per one centrifuge tube) containing 25% iodixanol-PBS-MK-Phenol Red (2.5 µl of 0.5% stock solution per ml of the iodixanol solution) were added to the same 50 ml tube. The dispensing of the second step was resumed as described above, followed by the third step, consisting of 10 ml (5 ml per one centrifuge tube) of 40% iodixanol-PBS-MK, and, finally, by 10 ml (5 ml per one centrifuge tube) of 60% iodixanol containing Phenol Red (at the same concentration as the 25% step, 0.01 µg/ml). The two imicrocapillary pipets then were carefully withdrawn and the tubes were filled with PBS-MK buffer. Therefore, each gradient consisted of (from the bottom up): 5 ml 60%, 5 ml 40%, 6 ml 25%, 9 ml of 15% iodixanol, the last density step containing 1 M NaCl.

Tubes were sealed and centrifuged in a Type 70 Ti rotor (Beckman Instruments, Somerset, N.J.) at 350,000×g for 1 h at 18° C. The Phenol Red serves to distinguish the alternating density steps. About 4 ml of the clear 40% step was aspirated after puncturing the tube on the side with a syringe equipped with an 18 gauge needle with the bevel uppermost. A similar amount was removed as 0.75 to 1 ml fractions upon harvest. The virus was further purified as described below and shown in FIG. 1.

5.1.1.6 Purification of rAAV Using CsCl Gradient Centrifugation

The rAAV-containing iodixanol fraction was further purified using a conventional CsCl gradient. To form the gradient 4.5 ml of virus in iodixanol were mixed with 35 ml of CsCl (1.37 g/ml in PBS), transferred into a Quick-Seal 25×89 mm centrifuge tubes (Beckman Instruments, Somerset, N.J.) and centrifuged in a Type 60 rotor (Beckman Instruments, Somerset, N.J.) at 214,800×g overnight at 18° C. The gradient was processed as described above.

5.1.1.7 Purification of rAAV Using Heparin Affinity Chromatography

The binding, washing and elution conditions were identical for all Heparin-ligand affinity media used. Typically, a pre-packed 2.5 ml Heparin agarose Type I column (Sigma Chemical, St. Louis, Mo.) was equilibrated with 20 ml of PBS-MK under gravity. Alternatively, the columns were placed inside 15 ml screw cap conical tubes (Sarstedt) and spun in a low speed centrifuge Type J6-HC (Beckman Instruments, Somerset, N.J.) at 200 rpm for 5 min. After each spin the flowthrough was discarded and fresh buffer was added to repeat the washing three more times. The iodixanol fraction containing virus was applied to the pre-equilibrated column under gravity and the column was washed with 10 ml of the PBS-MK buffer either under gravity or in the spin column mode. The rAAV was eluted with the same buffer containing 1 M NaCl under gravity. After applying the elution buffer, the first 2 ml of the eluant were discarded, and the virus was collected in the subsequent 3.5 ml of the elution buffer. Conventional Heparin columns that were not prepacked were loaded and eluted in a similar manner.

Alternatively, the Heparin agarose columns were placed into screw-type valves of the Visiprep Solid Phase Extraction (SPE) Vacuum Manifold (Supelco). The manifold valves were equipped with disposable Teflon valve liner guides, designed to eliminate the possibility of cross-contamination from one sample to the next in the same manifold port. Each guide was placed into 15 ml screw cap conical tube (Sarstedt) used as the collection vessel. This arrangement ensures that all surfaces that come in contact with the sample can be replaced following each chromatography. Chromatography was performed with house vacuum attached to the manifold's vacuum gauge, using less than 1 cm $H_2O$ (−1" Hg) vacuum. Precise flow control through each column was provided by rotating the independent, screw-type valves built into the cover. Up to 12 samples could be purified simultaneously using the 12-Port Model manifold.

For the ACTI-Disk 50 filter disk chromatography, the binding of the virus in 40% iodixanol was performed in the upward fashion, i.e., the flow of the solution was directed against gravity from the bottom part of the filter assembly towards the top using a peristaltic pump. Once applied, the filter assembly was turned up side down and chromatography was resumed in a regular downward fashion with gravity.

5.1.1.8 Purification of rAAV Using HPLC Chromatography

System Gold (Beckman Instruments, Somerset, N.J.) hardware installed inside a biosafety cabinet was used to further purify the iodixanol fraction of virus. Only biocompatible polyetheretherketone (PEEK) tubing and fittings were used to process the samples. The chromatography was monitored at 231 nm. The virus in 4 to 5 ml of iodixanol was directly loaded onto a column using 5 ml injection loop. When the volume of the sample exceeded 5 ml, multiple successive injections were performed, each followed by washing with 5 ml (injection loop dwell volume) of mobile phase. Two different columns were successfully used to purify the virus.

5.1.1.9 UNO™ S1 Cation-Exchange Chromatography

UNO™ S1 column (Bio-Rad Laboratories, Hercules, Calif.) contained "Continuous Bed" support (bed volume 1.3 ml) derivatized with strongly acidic negatively charged-$SO_3$ sulfonic groups. The column was pre-equilibrated with solvent A (PBS-MK buffer). The virus sample was loaded at 0.5 ml/min and the column was washed with solvent A until the iodixanol-induced absorption was reduced to near background levels. A 0–1 M gradient of NaCl in PBS-MK was applied over 36 min (15 column volumes) and the virus was eluted as a double UV absorption peak, which was collected manually.

5.1.1.10 Poros® HE Heparin Affinity Chromatography

POROS® HE/M heparin column (Boehringer Mannheim Biochemicals, Indianapolis, Ind.) contained particles coated with a crosslinked polyhydroxylated polymer (bed volume 1.7 ml) derivatized with heparin functional groups. The chromatography conditions were essentially the same as described for the UNO™ S1 column, except that a 0–0.5 M $Na_2SO_4$ in PBS-MK gradient was applied (15 column volumes) at a flow rate of 1 ml/min. A single UV absorption peak of a virus was collected manually.

5.1.1.11 Phenyl Sepharose Hydrophobic Interaction Chromatography

Phenyl Sepharose (Pharmacia Biotech) is a highly cross-linked agarose (6%, spherical) that is substituted with approximately 20 µmol (low sub) or 40 µmol (high sub) of phenyl per ml of gel. The column is equilibrated with a high ionic strength buffer (salt concentration just below that employed for salting out proteins, for example 1.7 M $(NH_4)_2SO_4$) at a flow rate of about 400 cm/h. The rAAV does not interact with the Phenyl Sepharose, and is eluted in the void volume of the column, while certain contaminating proteins interact with the column and are thus retained.

5.1.1.12 Concentration of rAAV

The virus was concentrated and desalted by centrifugation through a BIOMAX 100 K filter (Millipore, Bedford, Mass.) according to the manufacturer's instructions. The high salt buffer was changed by repeatedly diluting concentrated virus with Lactated Ringer's solution and repeating the centrifugation.

5.1.1.13 Quantitative Comprtitive PCR™ (QC-PCR™) Assay for Determining rAAV Physical Particles The purified viral stock was first treated with DNase I to digest any contaminating unpackaged DNA. Ten µl of a purified virus stock was incubated with 10 U of DNase I (Boehringer Mannheim Biochemicals, Indianapolis, Ind.) in a 100 μl reaction mixture, containing 50 mM Tris HCl, pH 7.5, 10 mM $MgCl_2$ for 1 h at 37° C. At the end of the reaction, 10 μl of 10×Proteinase K buffer (10 mM Tris HCl, pH 8.0, 10 mM EDTA, 1% SDS final concentration) was added, followed by the addition of 1 μl of Proteinase K (18.6 mg/ml, Boehringer Mannheim Biochemicals, Indianapolis, Ind.). The mixture was incubated at 37° C. for one h. Viral DNA was purified by phenol/chloroform extraction (twice), followed by chloroform extraction and ethanol precipitation using 10 μg of glycogen as a carrier. The DNA pellet was resuspended in 100 μl of $H_2O$ and dilutions were made to use in the QC-PCR™ assay.

The PCR™ reaction mixtures each contained 1 μl of the diluted viral DNA and two-fold serial dilutions of the internal standard plasmid DNA pdl-neo. The most reliable range of the dilution standard DNA was found to be between 1 and 100 pg. An aliquot of each reaction was then analyzed by 2% agarose gel electrophoresis, until two PCR™ products were resolved. The analog image of the ethidium bromide (EtBr)-stained gel was digitized using an ImageStore 7500 system (UVP). The densities of the target and competitor bands in each lane were measured using ZERO-Dscan Image Analysis System, version 1.0 (Scanalytics) and the respective ratios were plotted as a function of the standard DNA concentration. A ratio of 1, at which the number of viral DNA molecules equals the number of standard competitor DNA was used to derive the respective DNA concentration of the virus stock, which was the value of the line at the X intercept.

5.1.1.14 Infectious Center Assay to Determine rAAV Virus Titer

A modification of the previously published protocol (McLaughlin et al., 1988) was used to measure the ability of the virus to infect C12 cells (Clark et al., 1995), unpackage, and replicate. Briefly, C12 cells were plated in a 96-well dish at about 75% confluence and infected with Ad5 at the multiplicity of infection (M.O.I.) of 20. One μl of serially diluted rAAV to be titered was added to each well, whereupon cells were incubated for 42 h. Cells infected with rAAV-UF5 were visually scored using the fluorescence microscope. To calculate the titer by hybridization, cells were harvested and processed essentially as described earlier (McLaughlin et al., 1988).

5.1.1.15 Protein Concentration

The protein concentration in rAAV samples was determined using the NanoOrange™ Protein Quantitation Kit (Molecular Probes). The fluorescence in the sample was measured using the Laboratory Fluorometer Model TD-700 (Turner Designs). To estimate the purity of various virus fractions, virus was electrophoresed on 12% SDS acrylamide gels for 5 hours at 200 volts under standard buffer conditions and visualized by silver staining.

5.1.2 Results

The history of the rAAV as a gene delivery vector is not without controversy. While some investigators in the field report efficient rAAV-mediated transduction, others have found strong dependence of the transduction upon Ad helper virus contaminants (Ferrari et al., 1996), wt AAV contaminants (McLaughlin et al., 1988; Samulski et al., 1989) or mitotic or growth state of the cells being transduced (Russel et al., 1994). A pseudotaansduction artifact has been also reported when using crude rAAV viral preparations (Alexander et al., 1997).

Some of the variability in rAAV transduction in vivo is undoubtedly due to the intrinsic properties of the target cells. Some targets for example, do not have the high affinity heparin proteoglycan receptor (Summerford and Samulski, 1998) and others may be incapable of efficiently synthesizing the transcriptionally active form of the rAAV genome (Ferrari et al., 1996; Fisher et al., 1996). However, much of the variation is also due to the methods used for purifying rAAV and the contaminants that are present in the final preparation. In general, there has been a correlation between the success of AAV vectors and the ability to generate high-titer virus free of contaminants. Under optimal conditions, as few as 10–40 infectious particles of rAAV have been found to be sufficient to transduce one cell in vivo (Klein et al., 1998; Peel et al., 1997; Lewin et al., 1998).

Recent advances in design of wt AAV and mini Ad helper plasmids have made it possible to produce high-titer rAAV free of Ad contamination. Although the current transient transfection protocol for producing rAAV yields up to about $10^4$–$10^5$ rAAV particles per cell in crude lysates, relatively little attention has been paid to downstream purification. Most laboratories continue to use sequential CsCl centrifugation. Not only does it take several weeks to complete, it often results in loss of up to 90% of virus. Furthermore, the final stock is often contaminated with cell or serum proteins, which may compromise subsequent interpretation of the data by triggering an in vivo immune response. While the quality of such vector preparations may be useful in some laboratory studies, and perhaps even some additional preclinical applications, they are unsuitable for clinical studies using rAAV that require highly-purified vector stocks containing few if any contaminating substances.

5.1.2.1 Production of rAAV

To produce rAAV, the inventors used the transient Ca-phosphate-mediated co-transfection protocol, delivering three plasmids (rAAV vector pTR-UF5 (Zolotukhin et al., 1996), wt AAV helper pACG2 (Li et al., 1997) and Ad helper pXX6 (Xiao et al., 1998)). Alternatively the helper plasmid pDG was used to provide all genes required to propagate rAAV (Grimm et al., 1998). To streamline the protocol the $CaPO_4$/DNA precipitate was left in the media for the whole incubation period of 48 h. This did not compromise cell viability, but did increase the transfection efficiency at least two-fold. The transfection efficiency routinely reached 60% as judged by GFP fluorescence. After harvesting the cells, virus was extracted by freezing and thawing the cells and clarified by low speed centrifugation. The use of sonication, microfluidizing, and detergent extraction (for example, deoxycholate) did not appear to significantly increase the viral yield.

5.1.2.2 Iodixanol Density Step Gradient

Tamayose and co-authors have recently described a Cellulofine sulfate chromatography protocol as a method of purification and concentration of the rAAV from the crude lysate (Tamayose et al., 1996). However, using this method the inventors repeatedly failed to quantitatively bind rAAV in the crude lysate. It appeared that rAAV and cell proteins could form aggregates in lysate. These complexes fail to display uniform biochemical properties, which makes it difficult to develop a purification strategy. It also leads to poor recovery of the virus at all purification stages. Finally, this nonspecific interaction results in contamination with Ad proteins even after several rounds of CsCl gradient centrifugation.

The bulk purification of the crude is, therefore, a very important stage in rAAV purification. In the conventional protocol it is usually done by stepwise $NH_4SO_4$ precipitation (Snyder et al., 1996). Although this simple procedure could be used to concentrate the virus, the $NH_4SO_4$ precipitation makes a poor purification step. The residual ammonium sulfate salt in the protein pellet also interferes with subsequent ion-exchange chromatography procedure. The dialysis at this purification stage leads to the aggregation and precipitation of proteins, resulted in poor recovery of rAAV. The combination of $NH_4SO_4$ precipitation and hydrophobic interaction Phenyl-sepharose chromatography was also employed, although this approach also failed to produce a purified virus without sizeable loss of the infectivity. To solve the problem, the inventors introduced a new step into rAAV production protocol—iodixanol density gradient, which efficiently pre-purifies the virus from the crude cell extract.

Iodixanol is an iodinated density gradient media originally produced as an X-ray contrast compound for injection into humans and, as such, it has been subjected to rigorous screening and clinical testing. It is non-toxic to cells; indeed; cells can be grown in the presence of 30% iodixanol for 3 days with no subsequent effect on the viability of cells. Unlike CsCl and sucrose gradients commonly used for fractionating macromolecules, iodixanol solutions can be made iso-osmotic at all densities. This property makes iodixanol an ideal media for analysis and downstream purification steps. Because of its non-ionic and inert nature, electrophoretic analysis and virus infectivity assays can be carried out on gradient fractions directly in the presence of iodixanol. Since the viscosity of iodixanol solutions is also lower than those of sucrose of the same density, it is also possible to use the iodixanol fractions directly in subsequent chromatography purification steps without dialysis or dilution.

As mentioned earlier, rAAV aggregates with proteins in cell lysate, which changes its buoyant density and makes it distribute along the whole length of the gradient. This confounded initial attempts to purify rAAV using discontinuous iodixanol gradients. The inventors, however, devised a preformed multiple density step gradient that included 1 M NaCl in the first 15% step. The inventors reasoned that high concentrations of salt would destabilize ionic interactions between macromolecules, and reduce aggregation of rAAV particles with cell lysate material. High salt concentrations were excluded, however, from the rest of the iodixanol gradient in order to permit the virus to band under iso-osmotic conditions, which was important for subsequent purification steps.

The banding density of the purified rAAV-UF5 was approximately 1.415 g/ml, which corresponded to an about 52% concentration of iodixanol. The inventors therefore incorporated a 40% iodixanol step (1.21 g/ml) as a cut-off target step to accommodate rAAV/protein complexes trailing at slightly lower densities, followed by a 60% step that acts as a cushion for any rAAV containing a full length genome. To locate the 40% density step after the centrifugation, the inventors stained the upper 25% and lower 60% density steps with Phenol Red dye.

A plot of the refractive index at the end of a 1 hour run is shown in FIG. 2. rAAV was distributed through the 40% density step and could be recovered by inserting a syringe needle at about 2 mm below the 60%–40% density junction. The bulk of the rAAV bands within the 40% density step (fractions 5–8, FIG. 2). The heavy band at the 40%-to-25% density interface consisted mostly of cellular proteins and contained less than 5% of input rAAV, as judged by FCA. A small amount of the rAAV also bands at the 40%–60% density junction (fraction 5, FIG. 2). Approximately 75–80% of the rAAV in the crude lysate is recovered in the iodixanol fraction (Table I).

The nucleic acid/protein ratio in the rAAV-UF5 is different from wt AAV because of the size of the DNA packaged: 3400 bases in rAAV-UF5 vs. 4680 in wt AAV, or approximately 73% of the wt AAV size. Using the same protocol with no modifications, the inventors purified about 15 different rAAV vectors with the size of the packaged genome ranging from 3 to 5 kb. Regardless of the size, there was no substantial difference in the banding pattern of rAAV. Therefore, no modification of the protocol, accounting for the size of rAAV genome, is required.

To determine the resolving capacity of the iodixanol gradient, the inventors loaded into separate tubes virus-containing lysates obtained from $1.56 \times 10^8$ cells, $3.12 \times 10^8$ cells, or $4.68 \times 10^8$ cells, corresponding to 5, 10 or 15 large 15-cm culture plates, respectively. rAAV was aspirated as described, and aliquots of each sample that were equivalent to $1.73 \times 10^6$ cells were subjected to SDS-gel electrophoresis. The three viral capsid proteins VP1, VP2, and VP3 constituted the major protein species at all concentrations, even in the tube with the most concentrated lysate. In further studies, however, the inventors routinely loaded the lysate from 10 plates per gradient. In the scale-up protocol the viral lysate from $3.1 \times 10^9$ cell (one hundred 15-cm plates) could be pre-purified in one Ti 70 rotor during single one-hour run. Such run could potentially produce $10^{14}$ virus particles, or about $10^{12}$ infectious particles.

It is also possible to concentrate and purify rAAV from the media supernatant using the iodixanol gradient (FIG. 1). To do this, the inventors precipitated the bulk of proteins and virus from the media using conventional precipitation with 50% ammonium sulfate. The pellet was further resuspended in PBS-MK buffer and subjected to regular iodixanol gradient purification. This procedure, however, is optional, since at the time of harvesting cells 48 hours post-transfection the majority of the virus (about 90%) (Grimm et al, 1998; Xiao et al, 1998) is associated with cell pellet.

Iodixanol proved to be an excellent bulk purification method that accomplished at least three things. Crude lysate was purified by at least 100 fold and when Ad helper was present, Ad contamination was reduced by a factor of 100. The virus was concentrated in a non-ionic and relatively non-viscous medium that could be loaded on virtually any kind of chromatographic matrix. Finally, iodixanol prevented rAAV aggregation and the associated loss of virus that accompanies most other bulk purification and column chromatography methods. Typically, 70–80% of the starting infectious units are recovered following iodixanol gradient fractionation (Table I), and unlike other purification methods, this step was more reproducible.

5.1.2.3 Methods for Separating Adenovirus From rAAV

The production of rAAV by transient co-transfection with a mini Ad plasmid is an efficient but laborious protocol. Although it eliminates the problem of removing Ad virus from the rAAV crude lysate, it requires up to 1 mg of plasmid DNA (combined), for transfection of 10 plates. Furthermore, it is not readily amenable to the industrial large-scale production using suspension cell culture. An ideal production system would consist of rAAV proviral cell line, induced to rescue and replicate by infection with a helper virus carrying the rep/cap functions, such as an HSV amplicon (Conway et al, 1997), or rAd. For downstream purification the HSV helper could be separated from rAAV by simple filtration due to the considerable size difference (Conway et al, 1997) or by exposure to high salt. In case of Ad, rAAV is usually separated by a combination of CsCl gradient centrifugation and heat treatment, both approaches suffering from drawbacks. The inventors were interested in whether the newly introduced iodixanol gradient could be combined with ion exchange chromatography columns (FIG. 1) to separate rAAV and Ad without heat inactivation of the latter.

To address this issue, the inventors prepared pTR-UF6. This construct is identical to pTR-UF5 except that the , cDNA contains a Tyr-145-Phe mutation in the pTR-UFB background described previously (Zolotukhin et al., 1996) and fluoresces blue. At the time of co-transfection of 293 cells with pTR-UF6 and pDG, they were also infected with rAd-UF7 at an M.O.I. of 10. rAd-UF7 is a recombinant E1–E3 deleted Ad vector that contains the gfp/neo cassette from pTR-UF5 and fluoresces green. The use of these two constructs together permitted the monitoring of infections with rAAV (pTR-UF6) and rAd (rAD-UF7) in the same GFP fluorescence assay by scoring for blue or green cells. Cells infected with rAAV fluoresce blue, while cells infected with rAd (or both viruses) fluoresce green.

Cells transfected with pTR-UF6 and infected with rAD-UF7 were processed exactly as described for the purification of rAAV using iodixanol gradient. The gradient was fractionated after puncturing the bottom of the tube and 25 $\mu$l aliquots from each fraction were subjected to the SDS acrylamide gel electrophoresis and Western analysis with polyclonal anti-Ad antibodies. More than 99% of the Ad, as judged by the fluorescence assay, banded in the gradient with densities lower than 1.4 g/ml. rAAV, on the other hand, banded in fractions 5–8 (FIG. 2; densities of 1.4 to 1.415 g/ml) and were clearly separated from the Ad. The crude lysate contained $4.5\times10^{10}$ pfu of rAd-UF7 (as determined by the fluorescence cell assay). After the iodixanol gradient the titer of the rAd-UF7 dropped to $4.2-10^8$ pfu. Although iodixanol gradient efficiently separated rAAV/rAd mixture and reduced the titer of rAd by two logs, further purification steps were studied to further separate rAd.

To reduce Ad contamination further, column chromatography was used as a second step in purification following the iodixanol gradient. To compare the effectiveness of the various column chromatography steps, rAAV-UF5 was prepared from $1\times10^9$ cells as described above, using pDG helper plasmid. The crude lysate was purified using the iodixanol step gradient and virus-containing fractions were pooled. The pooled fractions were then split into equal portions and virus was purified using four different methods illustrated in FIG. 1: (1) CsCl density gradient centrifugation, (2) heparin affinity chromatography, (3) HPLC heparin affinity chromatography, and (4) HPLC cation exchange chromatography. The purification steps were monitored by measuring rAAV titers, both physical and infectious, as well as protein concentration in virus samples generated by each purification step (Table 1). For purposes of comparison, a second batch of virus was purified by the commonly used method of ammonium sulfate precipitation followed by two consecutive CsCl gradients (Table 1).

5.1.2.4 Heparin Affinity Chromatography

Heparinized supports have been successfully used for the purification of many heparin-binding macromolecules, including viruses such as CMV (Neyts et al., 1992). Heparin is the glucosaminoglycan moiety covalently bound to the protein core of proteoglycans (PG). It is closely related to heparan sulfate (HS), which constitutes the glycosaminoglycan (GAG) chain of the HS proteoglycan (HSPG). The latter has been shown to be a cell surface receptor mediating AAV infection (Summerford and Samulski, 1998). Covalent binding of heparin molecules to the matrix through its reducing end mimics the orientation of the naturally occurring GAGs (Nadcarni et al., 1994). To take advantage of the structural similarities between heparin and HS, heparin affinity chromatography was utilized to further purify rAAV.

Heparin is a heterogeneous carbohydrate molecule composed of long unbranched polysaccharides modified by sulfations and acetylations. The degree of sulfation strongly correlates with the virus-binding capacity of HS (Herold et al., 1995). It, therefore, was anticipated that hepaninized matrices from different vendors would display different affinity towards rAAV. Thus, to develop the method the inventors tested several heparin ligand-containing media, including ACTI-Disk 50 (Arbor Technologies, Inc.), Affi-Gel Heparin Gel (Bio-Rad Laboratories, Hercules, Calif.), Heparin-Agarose Type I, Heparin-Agarose Type II-S and, finally, Heparin Agarose Type III-S, the last three manufactured by Sigma Chemical, St. Louis, Mo. Although ACTI-Disk 50 was found to bind rAAV quantitatively, it was not used in the actual production protocol, since the manufacturer discontinued this product. Affi-Gel Heparin gel and Heparin Agarose Type III-S columns failed to bind at least 50% of the virus and, therefore, were excluded from further consideration. Heparin-Agarose Type I and Heparin-Agarose Type II-S pre-packed 2.5 ml columns were efficient in retaining and subsequently releasing rAAV. The Type II-S column, however, was found to be less selective, binding many cell proteins along with the virus. The Heparin-Agarose Type I was the best among those tested in terms of binding specificity and virus recovery, and was used in further studies as described below.

rAAV-UF5 purity at different stages of purification was analyzed by silver stained SDS acrylamide gel electrophoresis. The iodixanol-purified fraction prepared from cells transfected with pTR-UF5/pDG was directly applied to a Heparin-agarose Type I column and eluted with 1 M NaCl as described above. The 1 M NaCl fraction contained 35% of the input rAAV (Table 1), which was more than 95% pure, as judged by the silver stained SDS gel analysis. The Heparin-agarose affinity fraction of rAAV was consistently more pure than virus purified by the conventional protocol using ammonium sulfate, followed by two rounds of CsCl gradient centrifugation.

TABLE 1

SUMMARY OF RAAV-UF5 TITERS AND PROTEIN CONCENTRATION AT DIFFERENT STEPS OF THE PURIFICATION PROTOCOL[a]

| | Purification step | Particles by dot blot, $10^{11}$ | Particles by QC PCR ™, $10^{11}$ | Infectious particles by ICA, $10^9$ | Infectious particles by FCA, $10^9$ | Particle-to-infect. ratio[b] | Infect. Units per Cell[c] | Particle recovery, %[d] | Infectious particles yield, %[e] |
|---|---|---|---|---|---|---|---|---|---|
| 1 | 3 × Frz./thaw lys. | 57 | 103 | 69 | 62.7 | 90.8 | 209 | 100 | 100 |
| 2 | Iodixanol | 44 | 82 | 32.3 | 51 | 86 | 170 | 76 | 81 |
| 3 | Iodixanol/CsCl | 5.7 | 2.5 | 4 | 3.6 | 158 | 12 | 8.4 | 6 |

TABLE 1-continued

SUMMARY OF RAAV-UF5 TITERS AND PROTEIN CONCENTRATION AT DIFFERENT STEPS OF THE PURIFICATION PROTOCOL[a]

| Purification step | Particles by dot blot, $10^{11}$ | Particles by QC PCR™, $10^{11}$ | Infectious particles by ICA, $10^9$ | Infectious particles by FCA, $10^9$ | Particle-to-infect. ratio[b] | Infect. Units per Cell[c] | Particle recovery, %[d] | Infectious particles yield, %[c] |
|---|---|---|---|---|---|---|---|---|
| 4 Iodixanol/Heparin agarose | 20 | 63 | 32 | 35 | 56 | 117 | 35 | 56 |
| 5 Iodixanol/HPLC POROS ® HE/M | 15 | 16 | 12 | 20 | 73 | 67 | 26 | 32 |
| 6 Iodixanol/HPLC UNO ™ S1 | 19 | 13 | 20 | 20 | 95 | 67 | 33 | 32 |
| 7 2 × CsCl | 7 | 6 | 4.8 | 2.9 | 241 | 1 | | |

[a]The yield of rAAV and protein concentrations in each row are normalized to $3 \times 10^8$ cells (ten 15 cm plates).
[b]The particle-to-infectivity ratio was calculated using numbers obtained by dot blot assay and FCA.
[c]Calculated using FCA
[d]Calculated using dot blot assay 5.1.2.5 Purification of rAAV Using HPLC Chromatography Two different HPLC columns, UNO™ S1 and POROS® HE/M heparin, were tested to further purify the iodixanol fraction of rAAV (FIG. 3A and FIG. 3B). Both columns were successful in removing most of the protein contaminants that remained in the iodixanol fraction. The UNO™ S1 purification yielded rAAV-UF5 that was more than 99% pure as judged by SDS acrylamnide electrophoresis. Curiously two rAAV peaks were obtained during UNO™ S1 fractionation (FIG. 3B). Both peaks were found to contain rAAV that was indistinguishable both by SDS-gel electrophoresis analysis and by GFP fluorescence assay.

Both HPLC columns used in the study produced rAAV, comparable both in terms of purity and yield. POROS® HE/M column produced a slightly more infectious virus, which is not surprising, since the purification process involves binding to heparin, structurally similar to native AAV receptor. From the practical point of view, HPLC Heparin column is easier to use, it allows for a higher back pressure and, therefore, higher flow rates. It also cleared off iodixanol in the flowthrough much faster (30 min vs. 45 min, FIG. 3A and FIG. 3B). Finally, it performed consistently, producing essentially identical chromatograms for as many as 10 different virus runs (the maximum tried). This kind of performance is very important for GMP validation of a production protocol.

Having established that both the UNO™-S1 and POROS® HE/M columns could be used successfully to purify rAAV, the inventors determined whether they also would separate adenovirus from AAV in preparations grown in the presence of Ad virus. To this end, the rAAV-UF6/rAd-UF7 mixture (described above) was purified by iodixanol gradient centrifugation and then subjected to HPLC POROS® HE/M affinity chromatography under the conditions described above. The majority of the contaminating rAD-UF7 was found in the flowthrough. The peak of rAAV-UF6 contained $8 \times 10^5$ pfu of rAd, as compared to $3 \times 10^{10}$ infectious units (IU) of rAAV-UF6 particles. Thus, the rAd titer in the mixed stock was decreased from $4.5 \times 10^{10}$ in the crude lysate, to $4.2 \times 10^8$ in the iodixanol fraction, to the $8 \times 10^5$ after the HPLC affinity step. The same degree of separation was achieved with conventional chromatography using Heparin-agarose Type I. In contrast, UNO™ S1 cation exchange chromatography failed to separate rAd and rAAV. Additional data indicates that the mixture could be further separated using UNO™ Q1 anion exchange HPLC column.

5.1.2.6 Iodixanol Plus CsCl Density Gradient

The use of an iodixanol step gradient followed by a CsCl gradient was compared with the conventional use of two consecutive CsCl gradients (Table 1). The iodixanol plus CsCl protocol produced rAAV with purity that was comparable to iodixanol followed by column chromatography. Both methods produced rAAV that was significantly purer than virus that had undergone only two consecutive CsCl gradients. However the rAAV produced by conventional CsCl purification generally had higher particle-to-infectivity ratios (200–1000) than the methods described herein (Table 1). Furthermore, rAAV that had undergone even one CsCl centrifugation (Table 1, row 3) had a higher particle-to-infectivity ratio than virus that had not been exposed to CsCl (Table 1, rows 4–6). These observations suggest that treatment with CsCl leads to reduced viral infectivity.

Taken together, the data show that a combination of iodixanol plus heparin affinity chromatography (either heparin agarose or heparin HPLC) has unique advantages as a method for purifying rAAV. To compare this method directly with the current method for rAAV purification, a crude rAAV virus stock was prepared and the two methods of purification were compared side by side with the same starting material, i.e., ammonium sulfate fractionation followed by two CsCl gradients vs. iodixanol fractionation followed by heparin agarose chromatography (Table 2). A significant increase in recovery of vector was seen with the iodixanol/heparin protocol, resulting from an approximately 5 fold higher recovery of vector particles and over a 100 fold increase in infectivity. Expressed as the ratio of infectious particles to total particles, the virus prepared by CsCl centrifugation had a significantly higher ratio than virus prepared by the iodixanol protocol, approximately 1700 vs 67 (Table 1). Furthermore, as expected, the virus prepared by the conventional CsCl method was significantly less pure than that prepared by iodixanol/heparin.

TABLE 2

COMPARISON OF IODIXANOL/HEPARIN AGAROSE AND $NH_4SO_4$/CSCL PURIFICATION

| Purification | Particles by QC PCR ™ $10^{11}$ | Infectious Units by FCA $10^9$ | Particle-to-Infectivity Ratio |
|---|---|---|---|
| $NH_4SO_4$/2 × CsCl | 0.2 | 0.012 | 1667 |
| Iodixanol/Heparin Agarose | 1.0 | 1.5 | 67 |

Following iodixanol gradient fractionation, rAAV was sufficiently free of cellular protein such that it displayed reproducible chromatographic behavior during subsequent purification. Two types of columns have been identified that are capable of purifying rAAV approximately 10–100 fold, heparin sulfate and sulfate cation exchange resins. Both types of material could be used successfully in the HPLC format and displayed recoveries of 40–70% (Table 1). By contrast, CsCl purification of the iodixanol fraction resulted in the recovery of as little as 7% of the starting infectious units. Therefore, methods have been identified that increase the yield of infectious rAAV by at least ten-fold in this step.

Importantly, neither iodixanol fractionation nor column chromatography on heparin or cation exchange resins had a significant effect on the particle-to-infectivity ratio of rAAV. In contrast, the use of CsCl gradients generally had the detrimental effect of increasing the particle-to-infectivity ratio. If CsCl were the only method used for purification, the increase could be dramatic. The particle-to-infectivity ratios of rAAV that had been purified by iodixanol and heparin affinity ranged from as low as 26 to 73 (Table 1). The particle-to-infectivity ratio of rAAV that had been purified by iodixanol and CsCl was approximately 158 (Table 1). Finally, virus that had been purified only by ammonium sulfate fractionation and sequential CsCl centrifugation had particle-to-infectivity ratios of 241 to 1600 (Tables I and 2).

Thus, the inventors have identified methods for producing pure, high titer rAAV that are significantly better in yield and quality of material produced than the conventional methods currently in use. One of these methods, an iodixanol step gradient followed by a conventional heparin agarose column has consistently resulted in overall recoveries of greater than 50% of the starting material, and produces virus that is better than 99% pure, with particle-to-infectivity ratios less than 100:1. Furthermore, the method allows the purification of rAAV in one day.

5.1.2.7 Iodixanol Plus Heparin Affinity and Phenyl Sepharose Chromatography

The use of hydrophobic interaction chromatography (HIC) in the further purification of rAAV was investigated using Phenyl Sepharose gel (Pharmacia Biotech). rAAV that was initially purified on an iodixanol gradient and Heparin-Sepharose chromatography, as described above, was loaded onto a Phenyl Sepharose column. The rAAV does not interact with the Phenyl Sepharose, and is present in the supernatant (bulk purification) or elutes in the void volume (column purification). Several proteins present in the rAAV sample from the iodixanolheparin purification, in particular several proteins between 45 and 60 kDa and large proteins or aggregates of greater than about 116 kDa, interacted with the Phenyl Sepharose, and were retained in the gel.

5.1.2.8 Characterization of the Purified rAAV 5.1.2.8.1 rAAV Titering

An important index of virus quality is the ratio of the physical particles to the infectious particles in a given preparation. To characterize the purification steps and the quality of the virus obtained using different methods, the inventors used two independent assays to titer both physical and infectious rAAV particles. For physical particle titers, the inventors used a conventional dot-blot assay and a QC PCR™ assay. For the infectivity titer, the inventors used fluorescence cell assay (FCA), which scored for the expression of GFP, and infectious center assay (ICA). In order to avoid adventitious contamination of rAAV stocks with wt AAV, the use of wt AAV was eliminated from all protocols, including the ICA. For the ICA and FCA, the inventors used the C 12 cell line (Clark et al., 1995), which contains integrated wt AAV rep and cap genes. Ad5, which was used to co-infect C12 along with rAAV, was titered using the same C12 cell line in a serial dilution cytopathic effect (CPE) assay. The amount of Ad producing well-developed CPE in 48 h on C12 cells was used to provide helper function in both the ICA and FCA assays.

Both physical particle titers and infectious particle titers, each obtained by two independent titering methods, were generally in agreement, differing in most cases by a factor of 2 or less (Table 1). The particle-to-infectivity ratios ranged from 56 to 240. rAAV purified by iodixanol/Heparin affinity chromatography had the lowest (Table 1, Rows 4 and 5). rAAV purified exclusively by using CsCl centrifugation had the lowest infectivity, which is probably due to the deleterious effect of hyper-osmotic conditions of a gradient (Table 1, compare crude lysate in Row 1 and CsCl-purified virus, Rows 3 and 7). In extreme cases some CsCl-grade rAAV preparations had the respective ratios of 1000 or higher, while HPLC/heparin affinity purified stocks had ratios as low as 26.

5.1.2.8.2 rAAV Recovery

To compare the effectiveness of the column chromatography steps in a single study, rAAV-UF5 has been prepared from fifty 15 cm plates as described, using the pDG helper plasmid. The crude lysate was pre-purified using 5 tubes of iodixanol gradient and virus-containing fractions were pooled. The pooled fractions were then split and virus was purified using 5 different methods (FIG. 1). The inventors monitored the purification steps by measuring rAAV titers, both physical and infectious, as well as protein concentration in virus samples (Table 1). The total amount of the virus in the crude lysate was assumed to represent a 100% of virus, available for purification. The iodixanol gradient centrifugation step reduces the amount of protein in the sample 1,577 fold. Therefore, the degree of purification achieved at the first purification step is 1,214 times, if one takes into account the yield of viral particles.

5.1.2.8.3 Comparison of Helper Plasmids

Recently three independent groups described the construction of a new generation of helper plasmids, pXX6, (Xiao et al., 1998), pACG2 (Li et al., 1997), pDG (Grirrm et al., 1998) and pAdΔ (Salvetti, 1998), which modulate the synthesis of Rep78/68 and supply Ad helper functions from non-infectious, non-packagable mini-Ad plasmids. The inventors had the opportunity to evaluate side-by-side two systems, namely pACG2/pXX6 vs. pDG. In the studies both systems performed well, the pACG2/pXX6 yielding about $10^{15}$ particles of rAAV per ml of the purified stock per starting size run of ten 15 cm plates, with the "wild-type" replication-competent AAV contamination at about 3 to 4 logs lower than recombinant virus titer. pDG, on the other hand, produced somewhat lower titers, $3-4\times10^{12}$ particles/ ml, with no detectable "wt" AAV contamination, as judged by the ICA, done on 293 cells with Ad5 helper.

In conclusion, the developed protocol is very efficient, routinely yielding 30–40% of the total virus in the original crude lysate. The recovery of the virus in conventional CsCl protocol in the studies never exceeded 10%. The infectivity of iodixanol/heparin-purified virus is exceptional with the particle-to infectivity ratios consistently lower than 1:100. On the other hand, the respective ratio for the CsCl-purified virus stays within 1:200–1000 range. The inventors, therefore developed the method which increases the overall yield of the infectious rAAV by at least ten-fold.

In short, the inventors have developed protocols for the purification of rAAV that are versatile and efficient. rAAV, purified by any of these approaches, is highly infectious and practically free of contaminants. It is affordable for an average research lab (iodixanol/Heparin-agarose protocol), or it could be adopted for a GMP production facility (iodixanol/HPLC chromatography protocol). The use of such techniques make broader gene therapy applications of rAAV feasible.

6.0 REFERENCES

The following references, to the extent that they provide exemplary procedural or other details supplementary to those set forth herein, are specifically incorporated herein by reference.

Alexander, Russel, Miller, "Transfer of contaminants in Adeno-associated virus vector stocks can mimic transduction and lead to artifactual results," *Hum. Gene Ther.* 8:1911–1920, 1997.

Atchinson et al., *Science* 194:754–756, 1965.

Berns et al., In: *Virus Persistence*, Mehay et al. (Ed.), Cambridge Univ. Press, pp. 249–265, 1982.

Berns, Pinkerton, Thomas, Hoggan, "Detection of adeno-associated virus (AAV)-specific nucleotide sequences in DNA isolated from latently infected Detroit 6 cells," *Virol.* 68:556–560, 1975.

Buller, Janik, Sebring, Rose, "Herpes simplex virus types 1 and 2 completely help adenovirus-associated virus replication, *J. Virol.* 40(1):241–247, 1981.

Carter et al., In: *The Parvoviruses*, K. I. Berns (Ed.), Plenum, NY, pp. 67–128, 1983.

Carter et al., In: *The Parvoviruses*, K. I. Berns (Ed.), Plenum, NY, pp. 153–207, 1983.

Cheung, Hoggan, Hauswirth, Berns, "Integration of the adeno-associated virus genome into cellular DNA in latently infected human Detroit 6 cells," *J. Virol.* 33:739–748, 1980.

Chiorini et al., "High-efficiency transfer of the T cell co-stimulatory molecule B7-2 to lymphoid cells using high-titer recombinant adeno-associated virus vectors," *Hum. Gene Ther.* 6:1531–1541, 1995.

Clark, Sferra and Johnson, "Recombinant adeno-associated viral vectors mediate long-term transgene expression in muscle," *Hum. Gene Ther.* 8:659–669, 1997.

Clark, Voulgaropoulou, Fraley, Johnson, "Cell lines for the production of recombinant Adeno-associated virus," *Hum. Gene Ther.* 6:1329–1341. 1995.

Conway, Zolotukhin, Muzyczka, Hayward, Byrne, "Recombinant Adeno-associated virus Type 2 replication and packaging is entirely supported by a Hopes Simplex virus Type 1 amplicon expressing rep and cap," *J. Virol.* 71:8780–8789, 1997.

Cukor et al., In: *The Paroviruses*, K. I. Berns (Ed.), Plenum, NY, pp. 33–66, 1984.

Ferrari, Samulski, Shenk, Samulski, "Second-strand synthesis is a rate-limiting step for efficient transduction by recombinant adeno-associated virus vectors," *J. Virol.* 1996:3227–3234, 1996.

Fisher et al., "Transduction with recombinant adeno-associated virus for gene therapy is limited by leading-strand synthesis," *J. Virol.* 70:520–532, 1996.

Fisher et al., "Recombinant adeno-associated virus for muscle directed gene therapy," *Nat. Med.* 3:306–312, 1997.

Flannery, "Efficient photoreceptor-targeted gene expression in vivo by recombinant adeno-associated virus," *Proc. Natl. Acad. Sci. USA* 94:6916–6921, 1997.

Flotte, "Stable in vivo expression of the cystic fibrosis transmembrane conductance regulator with an adeno-associated virus vector," *Proc. Natl. Acad Sci. USA* 90:10613–10617, 1993.

Flotte et al., "A phase I study of an adeno-associated virus-CFTR gene vector in adult CF patients with mild lung disease," *Hum. Gene Ther.* 7:1145–1159, 1996.

Grimm, Kern, Rittner, Kleinschmidt, "Novel tools for production and purification or recombinant AAV vectors," *Hum. Gene Ther.* 9:2745–2760, 1998.

Handa, Shiroki, Shimojo, "Establishment and characterization of KB cell lines latently infected with adeno-associated virus type 1," *Virol.* 82:84–92, 1977.

Hardy, Kitamura, Harris-Stansil, Dai, Phipps, "Construction of adenovirus vectors through Cre-lox recombination," *J. Virol.* 71:1842–1849, 1997.

Heim and Tsien, "Engineering green fluorescent protein for improved brightness, longer wavelength and fluorescence resonance energy transfer," *Curr. Biol.* 6:178–182, 1996.

Hermonat and Muzyczka, "Use of adeno-associated virus as a mammalian DNA cloning vector: transduction of neomycin resistance into mammalian tissue culture cells," *Proc. Natl. Acad Sci. USA* 81:6466–6470, 1984.

Hermonat, Labow, Wright, Berns, Muzyczka, "Genetics of adeno-associated virus: isolation and preliminary characterization of adeno-associated virus type 2 mutants," *J. Virol.* 51:329–339, 1984.

Herold, Gerber, Polonsky, Belval, Shaklee, Holme, "Identification of structural features of heparin required for inhibition of Herpes Simplex virus Type 1 binding," *Virol.* 206:1108–1116, 1995.

Hoggan etal., In: *Proceeding of the Fourth Lepetit Colloquium*, Cacoyac, Mexico, North Holland, Amsterdam, pp. 243–249, 1972.

Hoggan, *Fed. Proc.* 24:248, 1965.

Inoue and Russell, "Packaging cells based on inducible gene amplification for the production of adeno-associated virus vectors," *J Virol.* 72:7024–7031, 1998.

Jooss, Yang, Fisher, Wilson, "Transduction of dendritic cells by DNA viral vectors directs the immune response to transgene products in muscle fibers," *J. Virol.* 727:4212–4223, 1998.

Kaplitt, "Long-term gene expression and phenotypic correction using adeno-associated virus vectors in the mammalian brain," *Nat. Genet.* 8:148–154, 1994.

Kessler, "Gene delivery to skeletal muscle results in sustained expression and systemic delivery of a therapeutic protein," *Proc. Natl. Acad. Sci. USA* 93:14082–14087, 1996.

Klein, "Neuron-specific transduction in the rat septohippocampal or nigrostriatal pathway by recombinant adeno-associated virus vectors," *Exper. Neurol.* 150:183–194, 1998.

Laughlin, Tratschin, Coon, Carter, "Cloning of infectious adeno-associated virus genomes in bacterial plasmids," *Gene* 23:65–73, 1983.

Lewin et al., "Ribozyme rescue of photoreceptor cells in a transgenic rat model of autosomal dominant retinitis pigmentosa," *Nat. Med.* 4:967–971, 1998.

Li, Samulski, Xiao, "Role for highly regulated rep gene expression in adeno-associated virus vector production, *J. Virol.* 71:5236–5243, 1997.

Lusby and Berns, "Mapping of the 5' termini of two adeno-associated virus 2 RNAs in the left half of the genome," *J. Virol.* 41:518–526, 1982.

McLaughlin, Collis, Hermonat, Muzyczka, "Adeno-associated virus general transduction vectors: analysis of proviral structures," *J. Virol.* 62:1963–1973, 1988.

Nadcarni, Pervin, Linhardt, "Directional immobilization of heparin to beaded supports," *Anal. Biochem.* 222:59–67, 1994.

Neyts, Snoeck, Schols, Balzarini, Esko, Van Schepdael, DeClercq, "Sulfated polymers inhibit the interaction of human cytomegalovirus with cell surface heparan sulfate," *Virology* 189:48–58, 1992.

Parks, Melnick, Rongey, Mayor, "Physical assay and growth cycle studies of a defective adeno-satellite virus," *J. Virol.* 1:171–180, 1967.

Peel, "Efficient transduction of green fluorescent protein in spinal cord neurons using adeno-associated virus vectors containing cell type-specific promoters," *Gene Ther.* 4:16–24, 1997.

Rose and Koczot, "Adenovirus-associated virus multiplication. VII. Helper requirement for viral deoxyribonucleic acid and ribonucleic acid synthesis," *J. Virol.* 10:1–8, 1972.

Rose, Berns, Hoggan, Koczot, "Evidence for a single-stranded adenovirus-associated virus genome: formation of a DNA density hybrid on release of viral DNA," *Proc. Natl. Acad. Sci. USA* 64:863–869, 1969.

Russel, Miller, Alexander, Adeno-associated virus vectors preferentially transduce cells in S phase," *Proc. Natl. Acad. Sci. USA* 91:8915–8919, 1994.

Salvetti, "Factors influencing recombinant adeno-associated virus production," *Hum. Gene Ther.* 9:695–706, 1998.

Samulski, Berns, Tan, Muzyczka, "Cloning of adeno-associated virus into pBR322: rescue of intact virus from the recombinant plasmid in human cells," *Proc. Natl. Acad Sci. USA* 79:2077–2080, 1982.

Samulski, Chang, Shenk, "Helper-free stocks of recombinant adeno-associated viruses: normal integration does not require viral gene expression," *J. Virol.* 63:3822–3828, 1989.

Samulski, Srivastava, Berns, Muzyczka, "Rescue of adeno-associated virus from recombinant plasmids: gene correction within the terminal repeats of AAV," *Cell* 33:135–143, 1983.

Snyder, "Persistent and therapeutic concentrations of human factor IX in mice after hepatic gene transfer of recombinant AAV vectors," *Nat. Genet.* 16:270–276, 1997.

Snyder, Xiao, Samulski, "Production of recombinant adeno-associated viral vectors," In: *Current Protocols in Human Genetics* (eds. Dracopoli et al), John Wiley, New York, 1996.

Srivastava, Lusby, Berns, "Nucleotide sequence and organization of the adeno-associated virus 2 genome," *J. Virol.* 45:555–564, 1983.

Summerford and Samulski, "Membrane-associated heparan sulfate proteoglycan is a receptor for adeno-associated virus type 2 virions," *J. Virol.* 72:1438–1445, 1998.

Tamayose, Hirai, Shimada, "TA new strategy for large-scale preparation of high-titer recombinant adeno-associated virus by using packaging cell lines and sulfonated cellulose column chromatography," *Hum. Gene Ther.* 7:507–513, 1996.

Tratschin, Miller, Carter, "Genetic analysis of adeno-associated virus: properties of deletion mutants constructed in vitro and evidence for an adeno-associated virus replication function," *J. Virol.* 51:611–619, 1984a.

Tratschin, West, Sandbank, Carter, "A human parvovirus, adeno-associated virus, as a eucaryotic vector: transient expression and encapsidation of the procaryotic gene for chloramphenicol acetyltransferase," *Mol. Cell. Biol.* 4:2072–2081, 1984b.

Wagner et al., "Efficient and persistent gene transfer of AAV-CFTR in maxillary sinus," *Lancet* 351:1702–1703, 1998.

Xiao, Li and Samulski, "Efficient long-term gene transfer into muscle tissue of immunocompetent mice by adeno-associated virus vector," *J. Virol.* 70:8090–8108, 1996.

Xiao, Li, Samulski, "Production of high-titer recombinant adeno-associated virus vectors in the absence of helper Adenovirus," *J. Virol.* 72:2224–2232, 1998.

Zolotukhin, Potter, Hauswirth, Guy, Muzyczka, "A humanized green fluorescent protein cDNA adapted for high level expression in mammalian cells," *J. Virol.* 70:4646–4654, 1996.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of isolating a recombinant adeno-associated virus comprising:
   (a) contacting a sample containing said virus with at least a first matrix comprising heparin, under conditions effective to permit binding of said virus to said at least a first matrix;
   (b) eluting said virus from said at least a first matrix;
   (c) contacting said virus eluted from said at least a first matrix with at least a first iodixanol gradient; and
   (d) collecting said virus from said at least a first iodixanol gradient.

2. The method of claim 1, wherein said at least a first matrix comprises heparin agarose type I.

3. The method of claim 1, wherein said at least a first matrix comprises heparin agarose type II-S.

4. The method of claim 1, further comprising: (a) contacting said virus collected from said at least a first iodixanol gradient with at least a first hydrophobic matrix under conditions effective to permit interaction of hydrophobic species with said at least a first hydrophobic matrix; and (b) collecting non-interacting virus from said at least a first hydrophobic matrix.

5. The method of claim 4, wherein said at least a first hydrophobic matrix comprises agarose.

6. The method of claim 5, wherein said at least a first hydrophobic matrix comprises phenyl-agarose.

7. The method of claim 1, further comprising contacting said virus collected from said at least a first iodixanol gradient with at least a second iodixanol gradient, and collecting said virus from said at least a second iodixanol gradient.

8. The method of claim 1, further comprising applying said virus collected from said at least a first iodixanol gradient to at least a first cesium chloride gradient, and collecting said virus from said at least a first cesium chloride gradient.

9. The method of claim 4, further comprising applying said virus collected from said at least a first hydrophobic matrix to at least a second iodixanol gradient, and collecting said virus from said at least a second iodixanol gradient.

10. The method of claim 8, further comprising applying the virus collected from said at least a first cesium chloride gradient to at least a second cesium chloride equilibrium density gradient, and collecting said virus from at least a first fraction of said at least a second cesium chloride equilibrium density gradient.

11. The method of claim 1, wherein said at least a first matrix is comprised within an HPLC column.

12. The method of claim 1, wherein said at least a first iodixanol gradient comprises an about 15% iodixanol step, and about 25% iodixanol step, and about 40% iodixanol step, or an about 60% iodixanol step.

13. The method of claim 1, wherein said at least a first iodixanol gradient further comprises NaCl.

14. The method of claim 1, wherein said virus is eluted from said at least a first matrix with a composition comprising NaCl.

15. The method of claim 14, wherein said virus is eluted from said at least a first matrix with a composition comprising at least about 1 M NaCl.

16. A method of isolating a recombinant adeno-associated virus, comprising the steps of:
   (a) contacting a sample containing recombinant adeno-associated virus with at least a first matrix comprising heparin under conditions effective to permit binding of said virus to said heparin;
   (b) removing non-bound species from said at least a first matrix;
   (c) eluting said recombinant adeno-associated virus from said at least a first matrix;
   (d) contacting said virus eluted from said at least a first matrix with at least a first iodixanol gradient; and
   (e) collecting said virus from said at least a first iodixanol gradient.

17. The method of claim 16, further comprising the steps of:
   (a) contacting said virus collected from said at least a first iodixanol gradient with at least a first hydrophobic matrix under conditions effective to permit interaction of hydrophobic species with said at least a first hydrophobic matrix; and
   (b) collecting the non-interacting virus from said at least a first hydrophobic matrix.

18. The method of claim 17, further comprising applying said virus collected from said at least a first hydrophobic matrix to at least a first cesium chloride gradient, and collecting from said gradient at least a first fraction comprising said virus.

19. A method for reducing or eliminating adenovirus from a recombinant adeno-associated virus composition contaminated with adenovirus, comprising:
   (a) applying said composition to at least a first matrix comprising heparin, under conditions effective to permit binding of said recombinant adeno-associated virus to said at least a first matrix;
   (b) eluting said recombinant adeno-associated virus from said at least a first matrix;
   (c) contacting said recombinant adeno-associated virus eluted from said at least a first matrix with at least a first iodixanol gradient; and
   (d) collecting said recombinant adeno-associated virus from said at least a first iodixanol gradient.

20. The method of claim 19, further comprising applying said recombinant adeno-associated collected from said at least a first iodixanol gradient to at least a first hydrophobic matrix and collecting said non-interacting recombinant adeno-associated virus from said matrix.

21. A method of purifying a population of adeno-associated virus particles, comprising the steps of:
   (a) contacting a sample containing a population of adeno-associated virus particles with at least a first matrix comprising heparin under conditions effective to permit binding of said adeno-associated virus particles to said heparin;
   (b) applying at least a first composition to said at least a first matrix to remove non-bound species;
   (c) eluting said population of adeno-associated virus particles from said at least a first matrix;
   (d) applying said population of adeno-associated virus particles eluted from said at least a first matrix to at least a first iodixanol gradient; and
   (e) collecting said population of adeno-associated virus particles from at least a first fraction of said at least a first iodixanol gradient.

22. The method of claim 21, further comprising the steps of:
   (a) contacting said population of adeno-associated virus particles collected from said at least a first fraction of said at least a first iodixanol gradient, with at least a first hydrophobic matrix under conditions effective to permit interaction of hydrophobic species with said at least a first hydrophobic matrix; and (b) collecting from said at least a first hydrophobic matrix a population of said adeno-associated virus particles.

23. The method of claim 21, wherein said population of adeno-associated virus particles comprises recombinant adeno-associated virus.

24. A kit comprising: (a) iodixanol; (b) at least a first heparin matrix; (c) at least a first hydrophobic matrix; and (d) instructions for isolating or purifying recombinant adeno-associated virus.

25. The kit of claim 24, further comprising cesium chloride.

26. The kit of claim 25, wherein said cesium chloride is formulated as a cesium chloride gradient.

27. The kit of claim 24, wherein said at least a first heparin matrix comprises heparin agarose type I or heparin agarose type II-S.

28. The kit of claim 24, wherein said at least a first hydrophobic matrix comprises phenyl-agarose.

* * * * *